(12) United States Patent
Binninger

(10) Patent No.: US 9,839,582 B2
(45) Date of Patent: Dec. 12, 2017

(54) STERILE CONNECTION SYRINGE ASSEMBLIES

(71) Applicant: Fenwal, Inc., Lake Zurich, IL (US)

(72) Inventor: Steven Binninger, Evanston, IL (US)

(73) Assignee: Fenwal, Inc., Lake Zurich, IL (US)

( * ) Notice: Subject to any disclaimer, the term of this patent is extended or adjusted under 35 U.S.C. 154(b) by 249 days.

(21) Appl. No.: 14/558,048

(22) Filed: Dec. 2, 2014

(65) Prior Publication Data

US 2016/0151573 A1   Jun. 2, 2016

(51) Int. Cl.
| | | |
|---|---|---|
| *A61M 5/24* | (2006.01) | |
| *A61J 1/20* | (2006.01) | |
| *A61M 5/32* | (2006.01) | |
| *A61M 5/31* | (2006.01) | |

(52) U.S. Cl.
CPC ........... *A61J 1/2089* (2013.01); *A61J 1/2096* (2013.01); *A61M 5/3243* (2013.01); *A61J 1/2027* (2015.05); *A61J 1/2044* (2015.05); *A61J 1/2065* (2015.05); *A61M 2005/312* (2013.01); *A61M 2005/3121* (2013.01)

(58) Field of Classification Search
CPC ...... A61J 1/2027; A61J 1/2044; A61J 1/2089; A61J 1/2096; A61M 2005/312; A61M 2005/3121; A61M 2005/3256; A61M 2005/3268; A61M 2005/1787; A61M 2005/3128; A61M 2005/31598

See application file for complete search history.

(56) References Cited

U.S. PATENT DOCUMENTS

| | | | | |
|---|---|---|---|---|
| 3,134,380 A | * | 5/1964 | Armao | A61M 5/001 604/198 |
| 3,354,881 A | * | 11/1967 | Bloch | A61M 5/326 215/247 |
| 3,968,195 A | | 7/1976 | Bishop | |
| 4,022,205 A | | 5/1977 | Tenczar | |
| 4,030,494 A | | 6/1977 | Tenczar | |
| 4,157,723 A | | 6/1979 | Granzow et al. | |
| 4,187,846 A | | 2/1980 | Lolachi et al. | |

(Continued)

FOREIGN PATENT DOCUMENTS

| | | |
|---|---|---|
| EP | 0507321 B1 | 10/1992 |
| JP | 61290035 | 12/1986 |

(Continued)

*Primary Examiner* — Emily Schmidt
(74) *Attorney, Agent, or Firm* — Cook Alex Ltd.

(57) ABSTRACT

Devices and methods are provided for sterile transfer of flowable material between a syringe and one or more flowable material receptacles or between a pair of receptacles. A syringe assembly may include a tip enclosure having a flexible shroud surrounding a syringe tip, with a shroud membrane associated with the distal end of the shroud to enclose the syringe tip. The shroud is deformable to move the tip toward the shroud membrane, which may be traversed by the tip to expose the tip for material transfers. A rigid connector may be positioned at the distal end of the shroud to securely connect the syringe assembly to a receptacle. The plunger and piston of the syringe assembly may include membranes to allow material transfer at the proximal end of the syringe assembly. An adaptor may also be provided for sterilely connecting a receptacle to a syringe or to another receptacle.

19 Claims, 13 Drawing Sheets

(56) References Cited

U.S. PATENT DOCUMENTS

| | | |
|---|---|---|
| 4,340,097 A | 7/1982 | Ammann et al. |
| 4,356,394 A | 10/1982 | Cobean et al. |
| 4,369,779 A | 1/1983 | Spencer |
| 4,434,822 A | 3/1984 | Bellamy et al. |
| RE32,056 E | 12/1985 | Granzow et al. |
| 4,564,054 A * | 1/1986 | Gustavsson ............ A61J 1/2096 141/329 |
| 4,611,643 A | 9/1986 | Beebe et al. |
| 4,673,400 A | 6/1987 | Martin |
| 4,753,697 A | 6/1988 | Shaposka et al. |
| 4,770,735 A | 9/1988 | Shaposka et al. |
| 4,786,286 A | 11/1988 | Cerny et al. |
| 4,793,880 A | 12/1988 | Shaposka et al. |
| 4,816,221 A | 3/1989 | Harvey et al. |
| 4,828,557 A | 5/1989 | Persidsky |
| 4,832,773 A | 5/1989 | Shaposka et al. |
| 4,864,101 A | 9/1989 | Shaposka et al. |
| 4,897,138 A | 1/1990 | Shaposka et al. |
| 4,913,756 A | 4/1990 | Shaposka et al. |
| 4,933,036 A | 6/1990 | Shaposka et al. |
| 4,978,446 A | 12/1990 | Lobdell |
| 5,009,645 A | 4/1991 | Silver et al. |
| 5,141,592 A | 8/1992 | Shaposka et al. |
| 5,156,701 A | 10/1992 | Spencer et al. |
| 5,158,630 A | 10/1992 | Shaposka et al. |
| 5,209,800 A | 5/1993 | Spencer et al. |
| 5,219,338 A * | 6/1993 | Haworth ............... A61M 5/326 604/198 |
| 5,244,522 A | 9/1993 | Spencer et al. |
| 5,248,359 A | 9/1993 | Shaposka et al. |
| 5,256,229 A | 10/1993 | Spencer |
| 5,256,845 A | 10/1993 | Schippers |
| 5,272,304 A | 12/1993 | Been et al. |
| 5,279,685 A | 1/1994 | Ivansons et al. |
| 5,342,345 A | 8/1994 | Spencer |
| D355,848 S | 2/1995 | Ivansons et al. |
| 5,397,425 A | 3/1995 | Ivansons et al. |
| D357,926 S | 5/1995 | Ivansons et al. |
| 5,518,575 A | 5/1996 | Watanabe |
| 5,525,186 A | 6/1996 | Ivansons et al. |
| 5,569,191 A * | 10/1996 | Meyer ................. A61F 9/0008 604/82 |
| 5,632,852 A | 5/1997 | Ivansons et al. |
| 5,674,333 A | 10/1997 | Spencer |
| 5,733,268 A | 3/1998 | Spencer |
| 5,802,689 A | 9/1998 | Sano |
| 5,855,731 A | 1/1999 | Spencer |
| 5,871,612 A | 2/1999 | Spencer |
| 5,919,173 A | 7/1999 | Spencer |
| 5,928,216 A | 7/1999 | Spencer |
| 6,020,574 A | 2/2000 | Ivansons |
| 6,026,882 A | 2/2000 | Yamada et al. |
| 6,071,690 A | 6/2000 | Spencer |
| 6,132,833 A | 10/2000 | Spencer |
| 6,177,652 B1 | 1/2001 | Ivansons |
| 6,341,637 B1 | 1/2002 | Yamada et al. |
| 6,348,049 B1 | 2/2002 | Spencer |
| 6,460,592 B1 | 10/2002 | Sano et al. |
| 6,463,979 B1 | 10/2002 | Sano et al. |
| 6,637,489 B1 | 10/2003 | Spencer |
| 6,705,372 B2 | 3/2004 | Sano et al. |
| 7,097,209 B2 | 8/2006 | Unger et al. |
| 7,119,305 B2 | 10/2006 | Sano et al. |
| 7,223,262 B2 | 5/2007 | Brehm et al. |
| 7,264,771 B2 | 9/2007 | Bilstad et al. |
| 7,371,305 B2 | 5/2008 | Sano et al. |
| 7,398,813 B2 | 7/2008 | Ivansons et al. |
| 7,484,529 B2 | 2/2009 | Yokota et al. |
| 7,657,996 B2 | 2/2010 | Sano et al. |
| 7,779,880 B2 | 8/2010 | Sano et al. |
| 7,828,788 B2 | 11/2010 | Brehm et al. |
| 7,938,454 B2 | 5/2011 | Buchanan et al. |
| 7,964,048 B2 | 6/2011 | Hlavinka et al. |
| 8,043,268 B1 * | 10/2011 | Marks ................... A61M 5/326 604/110 |
| 8,448,992 B2 | 5/2013 | Min et al. |
| 2002/0174956 A1 | 11/2002 | Sano et al. |
| 2004/0167004 A1 * | 8/2004 | Jorgensen ............. A61M 1/029 494/37 |
| 2006/0005371 A1 | 1/2006 | Sano et al. |
| 2006/0054275 A1 | 3/2006 | Sano et al. |
| 2006/0054613 A1 | 3/2006 | Sano et al. |
| 2006/0144525 A1 | 7/2006 | Sano et al. |
| 2007/0142960 A1 | 6/2007 | Bollinger et al. |
| 2007/0225673 A1 | 9/2007 | Brehm et al. |
| 2008/0009833 A1 | 1/2008 | Corbin et al. |
| 2009/0247961 A1 * | 10/2009 | Carlyon ................. A61M 5/28 604/237 |
| 2010/0137826 A1 | 6/2010 | Watts et al. |
| 2010/0249748 A1 * | 9/2010 | Szucs .................... A61M 5/326 604/506 |
| 2016/0106584 A1 * | 4/2016 | Andino ................. A61F 9/0017 604/87 |

FOREIGN PATENT DOCUMENTS

| | | |
|---|---|---|
| JP | 09150458 | 6/1997 |
| WO | WO8202528 | 8/1982 |
| WO | WO2008131442 | 10/2008 |

* cited by examiner

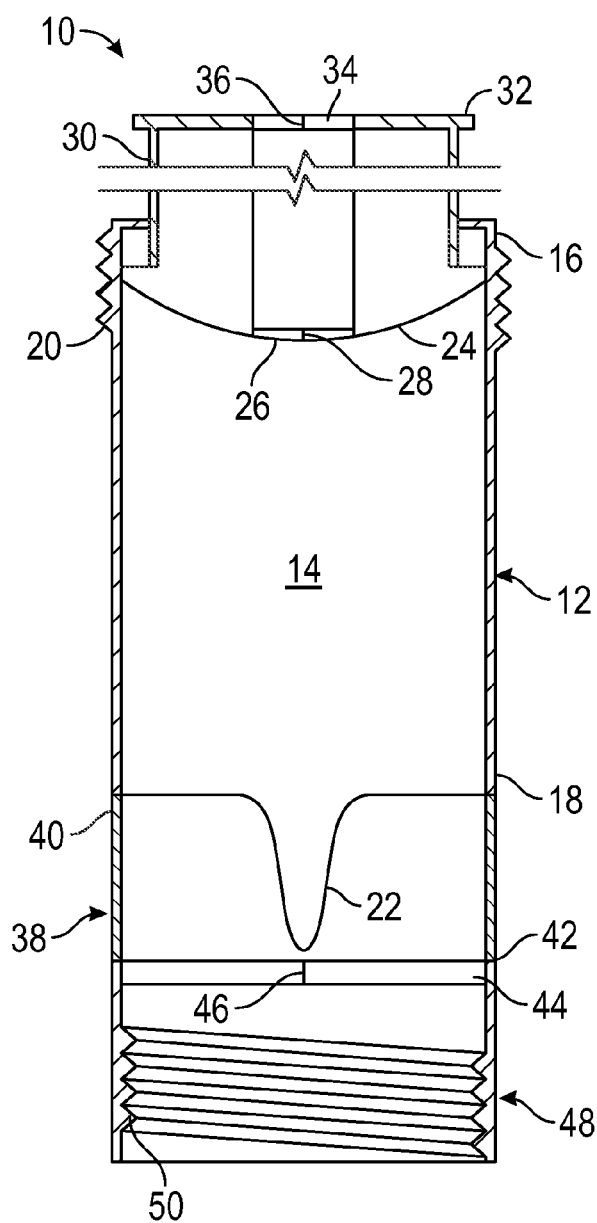
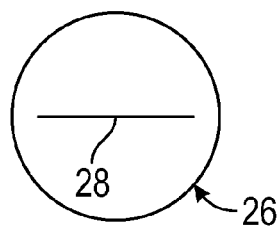
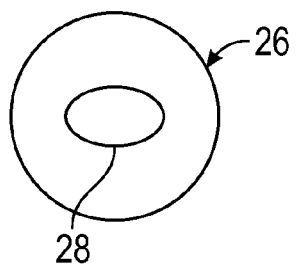
FIG. 1
FIG. 2
FIG. 3

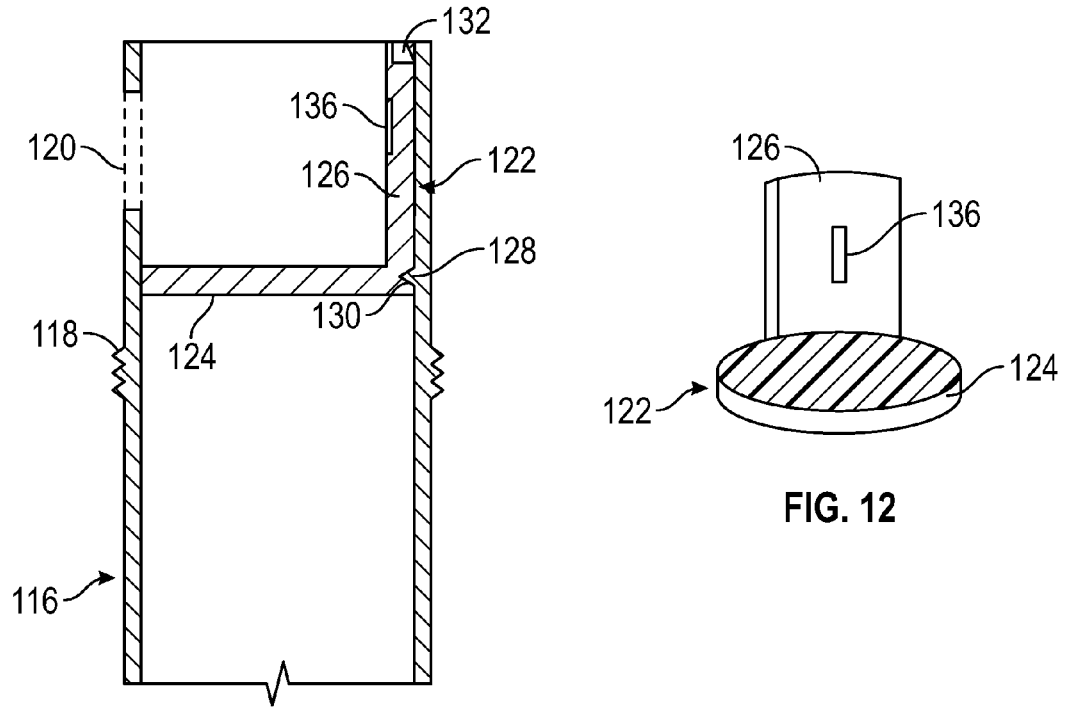
FIG. 11
FIG. 12
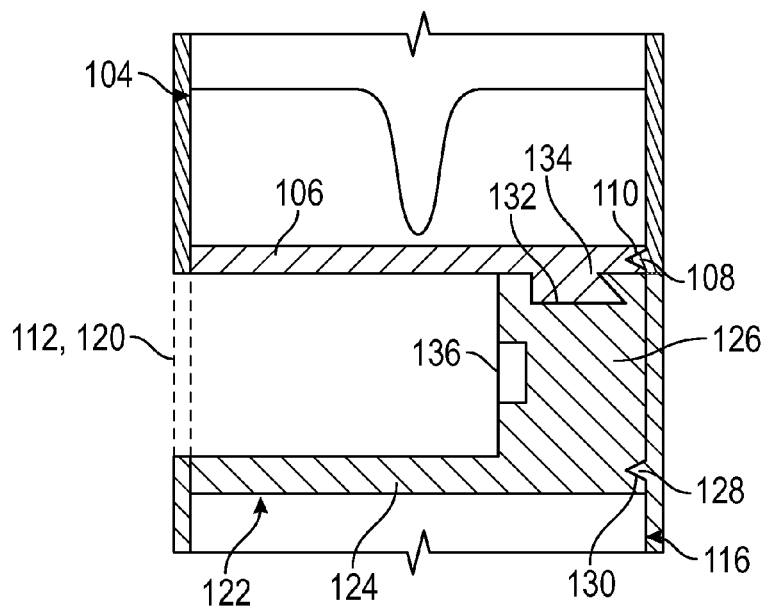
FIG. 13

STERILE CONNECTION SYRINGE ASSEMBLIES

BACKGROUND

Field of the Disclosure

The present invention relates generally to syringes, and more specifically, to syringes for sterile connection between two devices.

Description of Related Art

Pre-sterilized medical fluid flow systems are used in a wide variety of medical applications. In many situations these systems are assembled by joining together pre-sterilized subsystems or devices. This is often done using what is referred to a sterile docking device or method to preserve sterility of the assembled system.

Such sterile docking or joining systems may potentially be used in large scale manufacturing of medical fluid flow systems. They may also be used in a blood bank, drug manufacturing center, or other setting where the fluid flow system is assembled on a custom, as-needed basis for a particular patient, donor or procedure.

A number of different sterile docking or joining approaches have been heretofore used. One approach employs a pair of mating members, each having a facing surface. After the two members are joined, the docking device is exposed to radiant energy, causing the facing surfaces to melt and form a sterile weld, thereby defining a fluid pathway through the device. Exemplary systems employing a sterile weld are illustrated in U.S. Pat. Nos. 4,157,723 and 8,448,992, both of which are incorporated herein by reference.

It is also known to use sterilizing filters on the inlet flow line of a system that couples a pre-sterilized liquid container or the like to a separately pre-sterilized fluid flow tubing system. Such an arrangement is illustrated in U.S. Pat. No. 4,978,446, which is incorporated herein by reference.

Notwithstanding the above sterile docking devices and methods, there are situations in which it is impracticable to form a sterile weld between the two devices or to provide a filter therebetween, such that there remains a need for systems and methods for sterilely transferring fluid from one device to another in a different way.

SUMMARY

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

In one aspect, a syringe assembly includes a barrel extending between proximal and distal ends to define a chamber for containing flowable materials. A tip is associated with the distal end of the barrel. A piston is movable within the chamber, with a hollow plunger rod extending between proximal and distal ends and defining a lumen configured to accommodate the flow of the flowable materials, and with the distal end of the plunger rod being associated with the piston. The proximal end of the plunger rod is associated with a plunger positioned outside of the chamber. A two-way piston membrane is associated with the piston, at least partially aligned with the distal end of the plunger rod, and movable from a closed condition to an open condition to allow two way flow therethrough. A two-way plunger membrane is associated with the plunger, at least partially aligned with the proximal end of the plunger rod, and movable from a closed condition to an open condition to allow two way flow therethrough. At least a portion of the piston membrane and/or at least a portion of the plunger membrane is positioned within the lumen of the plunger rod. A flexible shroud extends between proximal and distal ends, with the proximal end of the flexible shroud being directly connected to the barrel and/or the tip. The flexible shroud surrounds the tip, with the distal end of the flexible shroud being positioned distally of the tip. A shroud membrane is associated with the distal end of the flexible shroud and is movable from a closed condition to an open condition.

In another aspect, a syringe assembly includes a barrel extending between proximal and distal ends to define a chamber for containing flowable materials. A tip is associated with the distal end of the barrel. A piston is movable within the chamber, with the distal end of a hollow plunger rod associated with the piston. The proximal end of the plunger rod is associated with a plunger positioned outside of the chamber. The plunger rod defines a lumen configured to accommodate the flow of the flowable materials between the proximal and distal ends of the plunger rod. A two-way piston membrane is associated with the piston, at least partially aligned with the distal end of the plunger rod, and movable from a closed condition to an open condition to allow two way flow therethrough. A two-way plunger membrane is associated with the plunger, at least partially aligned with the proximal end of the plunger rod, and movable from a closed condition to an open condition to allow two way flow therethrough, with at least a portion of the piston membrane and/or at least a portion of the plunger membrane being positioned within the lumen of the plunger rod.

BRIEF DESCRIPTION OF THE DRAWINGS

FIG. 1 is a cross-sectional side elevational view of a syringe assembly according to an aspect of the present invention;

FIG. 2 is a top plan view of a membrane of the syringe assembly of FIG. 1, with the membrane in a closed condition;

FIG. 3 is a top plan view of the membrane of FIG. 2, with the membrane in an open condition;

FIG. 11 is a cross-sectional side elevational view of the adaptor of FIG. 10;

FIG. 12 is a perspective view of a proximal keyed membrane of the adaptor of FIG. 10;

FIG. 13 is a cross-sectional side elevational view of a shroud or flat membrane of the syringe assembly of FIG. 9 connected to the proximal keyed membrane of the adaptor of FIG. 10;

DESCRIPTION OF THE ILLUSTRATED EMBODIMENTS

Figure 4:
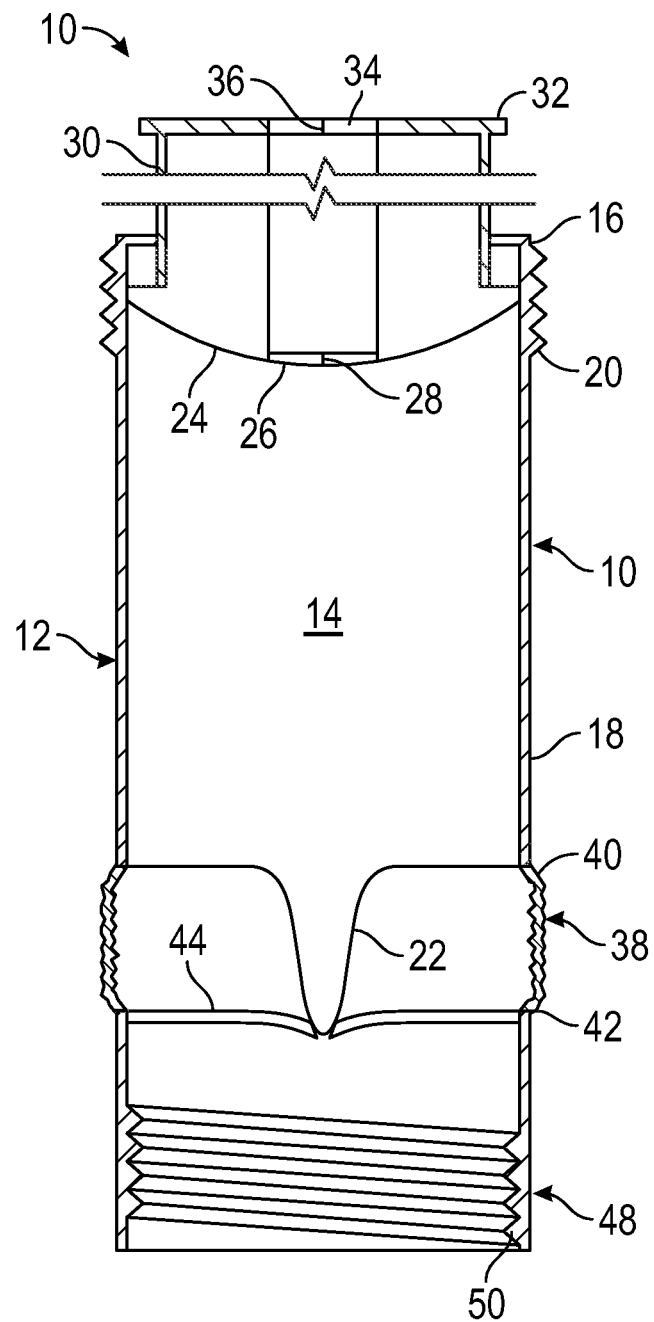
FIG. 4 is a cross-sectional side elevational view of the syringe assembly of FIG. 1, with a syringe tip extending through a shroud membrane.

The embodiments disclosed herein are for the purpose of providing a description of the present subject matter, and it is understood that the subject matter may be embodied in various other forms and combinations not shown in detail. Therefore, specific designs and features disclosed herein are not to be interpreted as limiting the subject matter as defined in the accompanying claims.

FIG. 1 shows an exemplary syringe assembly 10 according to an aspect of the present disclosure. The syringe assembly 10 has a barrel 12 defining a chamber 14 and extending between a proximal end 16 and a distal end 18. At and/or adjacent to its proximal end 16, the outer surface of the barrel 12 may include external threads 20 or any other suitable formation suitable for mating the barrel 12 to a device having internal threads or the like, as will be described in greater detail herein. While various structures and surfaces are described herein as having an internal thread/mating formation or an external thread/mating formation, it should be understood that such formations may be reversed, with an illustrated internal thread/mating formation being replaced with an external thread/mating formation and with an illustrated external thread/mating formation being replaced with an internal thread/mating formation.

An elongated luer or tip 22 is associated with the distal end 18 of the syringe barrel 12, being either integrally formed with the barrel 12 or otherwise secured thereto. The barrel 12 and tip 22 are preferably formed of a generally rigid, medical-grade material, such as glass or plastic or the like.

A piston 24 is positioned within the chamber 14, with an outer perimeter or surface of the piston 24 in contact with an inner surface of the chamber 14. The piston 24 is movable through the chamber 14 to draw a flowable material (which may include a fluid and/or a powder or granular material and/or any other material that is suitable for transfer via the devices described herein) into or expel a flowable material from the chamber 14. In particular, the piston 24 may be moved toward the syringe tip 22 to expel a flowable material from the chamber 14 via the tip 22 or moved away from the tip 22 to draw a flowable material into the chamber 14 via the tip 22. The piston 24 is preferably formed of a generally rigid, medical-grade material, such as plastic or the like.

In one embodiment, the piston 24 includes a membrane 26, which is referred to herein as the piston membrane. The piston membrane 26 may be a substantially flat or planar structure with a circular perimeter (as in FIGS. 2 and 3), although it is also within the scope of the present disclosure for the piston membrane 26 to be non-planar (e.g., with a varying or non-uniform thickness) and/or have a non-circular perimeter shape. Preferably, the piston membrane 26 is formed of a generally flexible or deformable material, such as rubber or another elastomeric material or the like. For example, in one embodiment, the piston membrane 26 may be similarly configured to the slit membrane of the INTERLINK® injection site of Baxter Healthcare Corporation of Deerfield, Ill.

Figure 8:
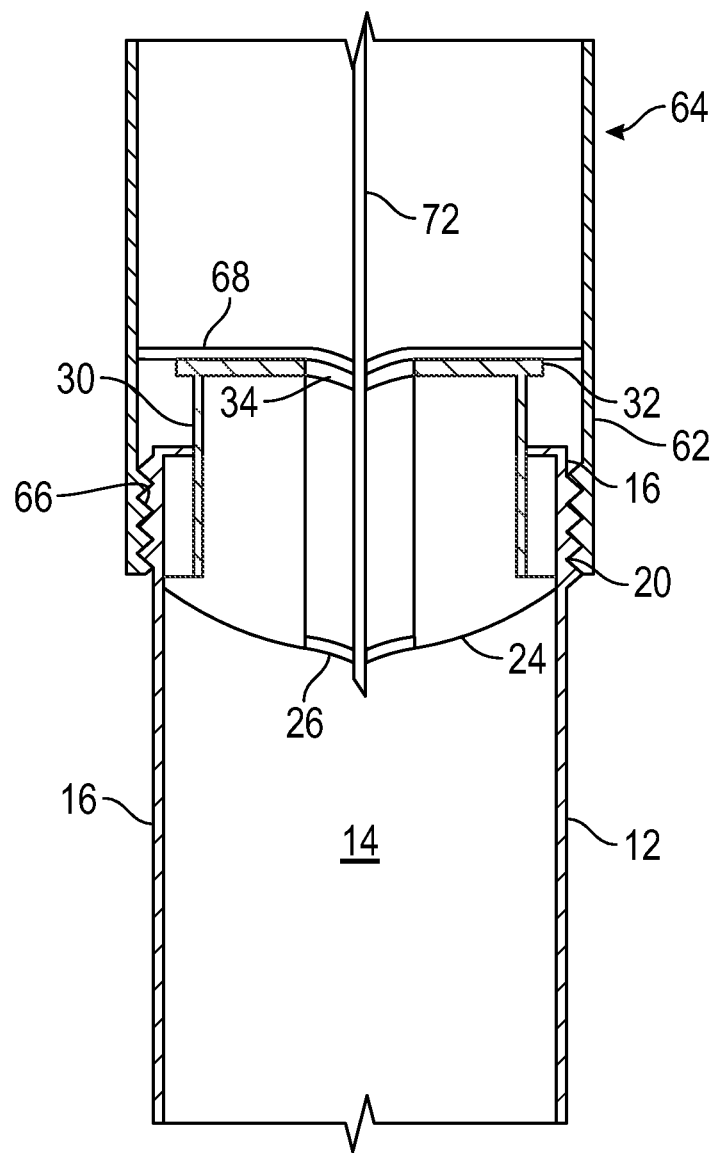
FIG. 8 is a cross-sectional side elevational view of the device and syringe assembly of FIG. 7, with the device secured to the syringe assembly for material transfer therebetween.

The piston membrane 26 is preferably movable between a closed condition (FIG. 2) and an open condition (FIG. 3), but it is also within the scope of the present disclosure for the piston membrane 26 to be moved only from the closed condition to the open condition. In the closed condition, flowable material is prevented from moving through the piston membrane 26, whereas flowable material may move through the piston membrane 26 when it is in the open condition. The piston membrane 26 may be variously configured, but in the illustrated embodiment, the piston membrane 26 includes a slit 28 that, by default, assumes the closed condition of FIG. 2, but can be moved or deformed into the open condition of FIG. 3 by insertion of a flowable material transfer device (e.g., a needle or syringe tip) or a portion thereof at least partially into the slit 28 (FIG. 8). If the piston membrane 26 is formed of a resilient material, then the slit 28 may tend to return to the closed condition after the flowable material transfer device or portion thereof is removed from the slit 28. In other embodiments, the slit 28 may be replaced by a frangible section or the like, which may be broken to move the piston membrane 26 from a closed condition to an open condition, without allowing the piston membrane 26 to be returned from the open condition to the closed condition. In yet another embodiment, the piston membrane 26 may be configured to move only from an open condition to a closed condition, which may be useful in drawing a flowable material into the chamber 14 (through the open piston membrane 26) and then closing or sealing the piston membrane 26.

The distal end of a plunger rod 30 is associated with the piston 24, with a proximal end of the plunger rod 30 being associated with a plunger 32 positioned outside of the syringe chamber 14. The plunger rod 30 and plunger 32 may be formed of a generally rigid, medical-grade material, such as plastic or the like. The piston 24, plunger rod 30, and plunger 32 move as a single unit (referred to herein as a piston assembly), with the plunger 32 being moved distally to advance the piston 24 toward the syringe tip 22 to temporarily decrease the effective volume of the chamber 14 and eject flowable material from the syringe chamber 14 via the tip 22 if there is such flowable material in the chamber 14. The plunger 32 may be moved proximally to move the piston 24 through the syringe chamber 14 away from the tip 22 to temporarily increase the effective volume of the chamber 14 and draw flowable material into the syringe chamber 14 via the tip 22 if there is such material in fluid communication with the tip 22. The plunger rod 30 may be removably secured to the piston 24 and/or the plunger 32 (e.g., by a threaded connection) or fixedly secured to either or both.

For embodiments in which the piston 24 includes a piston membrane 26, the plunger rod 30 may be hollow, with the distal end of the plunger rod 30 being aligned with at least a portion of the piston membrane 26. The plunger 32 may have a plunger membrane 34 configured to move from a closed condition (as in FIGS. 1 and 2) to an open condition (as in FIGS. 3 and 8) or, more preferably, between open and closed conditions. The plunger membrane 34 may be provided in accordance with the foregoing description of the piston membrane 26 (e.g., with a slit 36) or may be differently configured. It may be advantageous for the plunger membrane 34 and the piston membrane 26 to be substantially identical.

Figure 7:
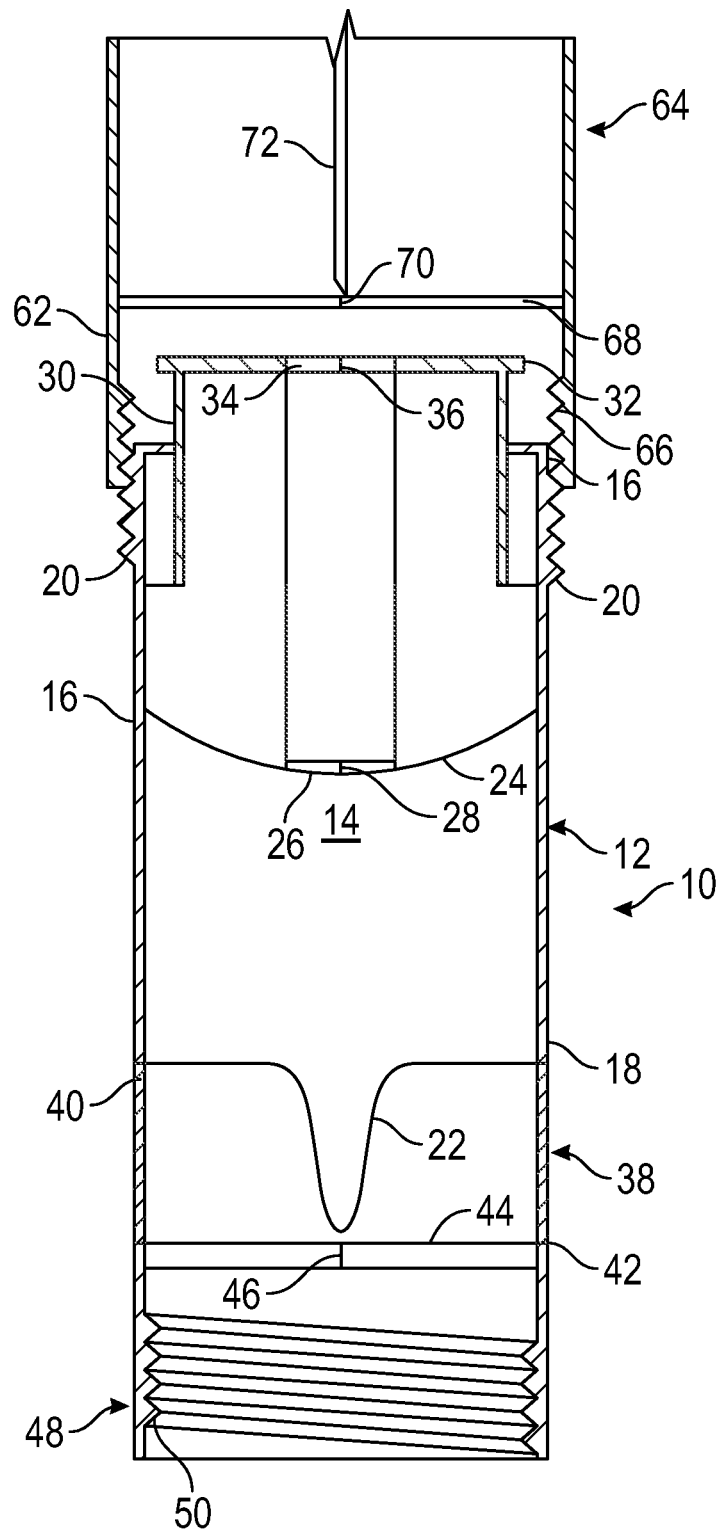
FIG. 7 is a cross-sectional side elevational view of a device being moved into engagement with the syringe assembly of FIG. 1 for material transfer therebetween.

The proximal end of the plunger rod 30 may be aligned with at least a portion of the plunger membrane 34. By such a configuration, a flowable material may flow through the piston assembly between a location proximal to the plunger 32 (e.g., a flowable material container) and the syringe chamber 14 when the piston membrane 28 and the plunger membrane 34 are in the open condition. This aspect of the present disclosure is illustrated in FIGS. 7 and 8, and will be described in greater detail herein in terms of an exemplary use of the syringe assembly 10.

A shroud 38 may be associated with the distal end 18 of the barrel 12 and/or the syringe tip 22. In contrast to the barrel 12 and tip 22, which are preferably formed of a generally rigid or inflexible material, the shroud 38 may be formed of a generally flexible or deformable material, such as rubber or a medical-grade elastomeric material or the like. The shroud 38 extends between proximal and distal ends 40 and 42 and is configured to surround or encircle the tip 22 (e.g., by being formed as a generally tubular structure). As in the illustrated embodiment, it may be advantageous for the shroud 38 to be relatively thin (e.g., with a thickness on the order of one millimeter), with an outer surface of the shroud 38 having a diameter substantially equal to the diameter of the outer surface of the barrel 12 and the proximal end 40 of the shroud 38 secured to the distal end 18 of the barrel 12, such that the shroud 38 effectively serves as a proximal extension of the barrel 12. In other embodiments, the shroud 38 may have a greater diameter than the barrel 12 or a smaller diameter than the barrel 12.

The distal end 42 of the shroud 38 is positioned distally of the tip 22 and may have a shroud membrane 44 associated with it. The shroud 38 and the shroud membrane 44 (collectively referred to herein as the "tip enclosure") combine to define a sterile enclosure in which at least a portion of the syringe tip 22 is positioned prior to use of the syringe assembly 10. The tip enclosure allows the tip 22 to remain sterile prior to use of the syringe assembly 10 without the need for separate packaging. Similar to the piston membrane 26 and the plunger membrane 34, the shroud membrane 44 may be configured to move from a closed condition (as in FIGS. 1 and 5) to an open condition (as in FIGS. 4 and 6) or, more preferably, between open and closed conditions. The shroud membrane 44 may be provided in accordance with the foregoing description of the piston membrane 26 (e.g., with a slit 46) or may be differently configured.

Figure 5:
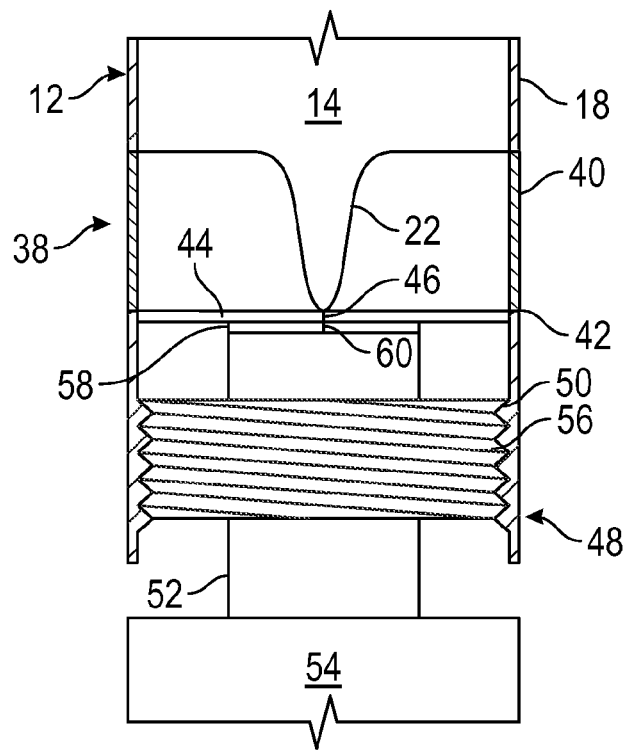
FIG. 5 is a detail view of the distal end of the syringe assembly of FIG. 1 connected to a flowable material receptacle for material transfer therebetween.
Figure 6:
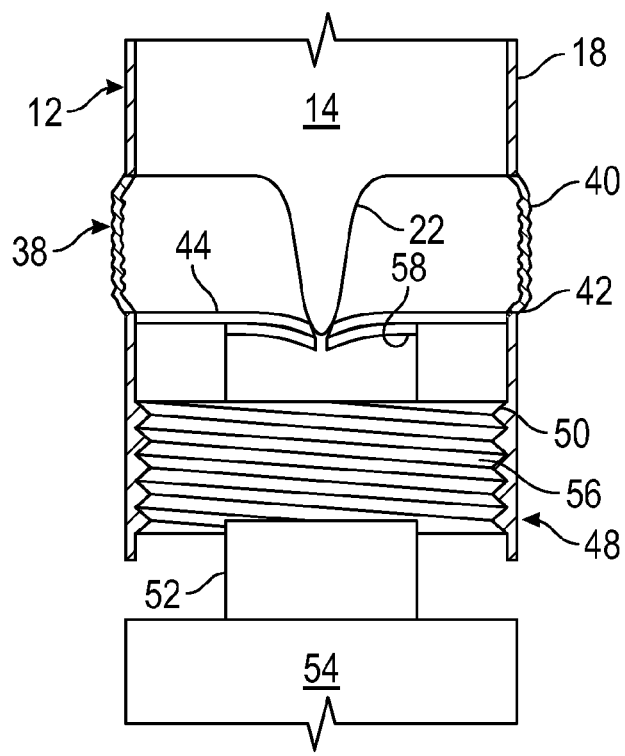
FIG. 6 is a detail view of the distal end of the syringe assembly of FIG. 1 connected to a flowable material receptacle for material transfer therebetween, with a syringe tip extending through a shroud membrane.

A generally rigid connector 48 may be associated with the distal end 42 of the shroud 38 and/or the shroud membrane 44. It should be understood that it may be preferable for the syringe assembly 10 to include a distal connector 48 if it is provided with a tip enclosure, but it is also within the scope of the present disclosure for a syringe assembly to include a tip enclosure without a distal connector. If provided, the connector 48 may be formed of the same material as the barrel 12 or any other suitable (preferably medical-grade) material. As in the illustrated embodiment, it may be advantageous for the connector 48 to be relatively thin (e.g., with a thickness that is comparable to the thickness of the shroud 38), with an outer surface of the connector 48 having a diameter substantially equal to the diameter of the outer surface of the shroud 38, such that the connector 48 effectively serves as a proximal extension of the shroud 38. In other embodiments, the connector 48 may have a greater diameter than the shroud 38 (in which case the connector 48 may be secured to an outer surface of the shroud 38) or a smaller diameter than the shroud 38 (in which case the proximal end of the connector 48 may be secured to the shroud membrane 44). The inner surface of the connector 48 may include internal threads 50 or any other suitable formation suitable for mating the connector 48 to a device having external threads or the like, as illustrated in FIGS. 5 and 6, and as will be described in greater detail herein.

While the illustrated embodiment includes both a tip enclosure and a piston assembly having a pair of membranes 26 and 34 and a hollow plunger rod 30, it is within the scope of the present disclosure for a syringe assembly to include only one of these features. In embodiments in which a tip enclosure is provided, the shroud membrane 44 may be pressed against the mating port 52 of a flowable material receptacle 54 (FIGS. 5 and 6). The configuration of the port 52 of the flowable material receptacle 54 depends on the configuration of the shroud 38, shroud membrane 44, and (if provided) distal connector 48. In the illustrated embodiment, the port 52 is configured as an INTERLINK® injection site, with a generally tubular body having external threads 56 and a port membrane 58 having a slit 60 that may be moved between a closed condition and an open condition (as described above with respect to the piston membrane 26). In other embodiments, the port 52 may be differently configured to complement the configuration of the shroud 38, shroud membrane 44, and (if provided) distal connector 48.

In use, the syringe assembly 10 is advanced toward the port 52 so as to bring the internal threads 50 of the connector 48 into engagement with the external threads 56 of the port 52. The syringe assembly 10 and flowable material receptacle 54 are then rotated with respect to each other to mate the threads 50 and 56 together. In one embodiment, the shroud 38, shroud membrane 44, and connector 48 are configured to place the shroud membrane 44 into contact with the port membrane 58 when the syringe assembly 10 has been fully secured to the port 52, as shown in FIG. 5. In other embodiments, the membranes 44 and 58 may move into contact with the syringe assembly 10 only partially secured to the port 52 or for the membranes 44 and 58 to be spaced apart (preferably only a small distance) when the syringe assembly 10 has been fully secured to the port 52.

With the syringe assembly 10 at least partially secured to the flowable material receptacle 54, the syringe tip 22 may be advanced distally toward the flowable material receptacle 54. The flexible or deformable shroud 38 allows the syringe tip 22 to move with respect to the flowable material receptacle 54, as well as the shroud membrane 44, with the shroud 38 flexing or deforming from an initial state (FIG. 5) to an at least partially deformed or flexed state (FIG. 6). The tip 22 approaches the shroud membrane 44 and the shroud 38 continues deforming until the tip 22 engages the shroud membrane 44. Continued distal movement of the syringe tip 22 with respect to the shroud membrane 44 presses the tip 22 into the slit 46 of the shroud membrane 44, thereby moving the shroud membrane 44 to an open condition, which allows a flowable material to pass through the shroud membrane 44. If the port membrane 58 is substantially flush with the shroud membrane 44, then distal movement of the syringe tip 22 moves the port membrane 58 to an open condition sequentially, but substantially simultaneously with the shroud membrane 44 (FIG. 6). On the other hand, if there is a small separation between the membranes 44 and 58, then distal relative movement of the syringe tip 22 will move the shroud membrane 44 into an open condition, advance the syringe tip 22 across the gap between the membranes 44 and 58, and then move the port membrane 58 into an open condition.

With the syringe tip 22 extending through the two membranes 44 and 58 and at least partially positioned within the port body, a flowable material may be transferred between the syringe assembly 10 and the flowable material receptacle 54. If flowable material is to be transferred from the syringe assembly 10 to the flowable material receptacle 54, the plunger 32 may be moved distally into the barrel 12 to eject flowable material out of the tip 22 and into the flowable material receptacle 54. If flowable material is to be transferred from the flowable material receptacle 54 to the syringe assembly 10, the plunger 32 may be moved proximally through the barrel 12 to create a vacuum that draws flowable material from the flowable material receptacle 54 into the barrel 12 via the syringe tip 22. In either case, it will be seen that the material transfer between the syringe assembly 10 and the flowable material receptacle 54 is sterile, without requiring a sterile weld or a filter or disinfection of either mating surface.

After material transfer, the syringe assembly 10 may be detached from the flowable material receptacle 54 by reverse relative rotation of the two to disengage the mating threads 50 and 56. It may be advantageous to move the syringe tip 22 proximally away from the flowable material receptacle 54 to move the membranes 44 and 58 into a closed condition and reposition the syringe tip 22 inside of the tip enclosure prior to disconnecting the connector 48 from the port 52.

While the foregoing procedure included a distal connector 48 of the syringe assembly 10 being secured to the port 52, a similar flowable material transfer may be carried out using a syringe assembly having a tip enclosure without an associated distal connector. In such an embodiment, the shroud membrane 44 is aligned with and pressed flat against the port membrane 58. The syringe tip 22 may then be advanced distally with respect to the flowable material receptacle 54 (causing the shroud 38 to at least partially deform or flex or collapse) until the syringe tip 22 traverses the membranes 44 and 58 and enters into the body of the port 52, at which point flowable material may be transferred between the syringe assembly 10 and the flowable material receptacle 54 as described above.

In embodiments in which piston and plunger membranes 26 and 34 are provided, the plunger 32 may be mated or associated with the port 62 of a flowable material receptacle 64 (FIGS. 7 and 8). The configuration of the port 62 of the flowable material receptacle 64 depends on the configuration of the piston assembly and proximal section of the syringe barrel 12. In the illustrated embodiment, the piston assembly and proximal section of the syringe barrel 12 combine to be configured as an INTERLINK® injection site, with the proximal section of the barrel 12 having external threads 20 and the plunger membrane 34 having a slit 36 that may be moved between a closed condition and an open condition (as described above). In such an embodiment, the port 62 of the flowable material receptacle 64 may be provided as a generally rigid, tubular body with internal threads 66. A port membrane 68 may be positioned proximally of the internal threads 66, with the port membrane 68 having a slit 70 or otherwise being configured to move from a closed condition (FIG. 7) to an open condition (FIG. 8) or between closed and open conditions. The flowable material receptacle 64 may further include a cannula or flowable material access member 72 positioned proximally of the port membrane 68 and configured to extend through the hollow plunger rod 30 (FIG. 8), as will be described in greater detail. In other embodiments, the port 62 may be differently configured to complement the configuration of the piston assembly and proximal section of the barrel 12.

In use, the syringe assembly 10 is advanced toward the port 62 of the flowable material receptacle 64 so as to bring the internal threads 66 of the port 62 into engagement with the external threads 20 of the syringe barrel 12 (FIG. 8). The syringe assembly 10 and flowable material receptacle 64 are then rotated with respect to each other to mate the threads 20 and 66 together. In one embodiment, the piston assembly and proximal section of the barrel 12 are configured to place the plunger membrane 34 into contact with the port membrane 68 when the syringe assembly 10 has been fully secured to the port 62, as shown in FIG. 5. In other embodiments, the membranes 34 and 68 may move into contact with the syringe assembly 10 only partially secured to the port 62 or for the membranes 34 and 68 to be spaced apart (preferably only a small distance) when the syringe assembly 10 has been fully secured to the port 62.

With the syringe assembly 10 at least partially secured to the flowable material receptacle 64, the cannula or flowable material access member 72 may be advanced distally toward the syringe assembly 10. This may be achieved by providing a cannula or flowable material access member 72 that is movable with respect to the port membrane 68, for example if a syringe assembly 10 according to the present disclosure is provided as the proximal flowable material receptacle 64. Alternatively, the flowable material receptacle 64 may be configured such that the cannula or flowable material access member 72 extends through the piston and plunger membranes 26 and 34 and plunger rod 30 when the port 62 has been secured to the syringe assembly 10.

Distal movement of the cannula or flowable material access member 72 presses its tip or distal end into the slit 70 of the port membrane 68, thereby moving the port membrane 68 to an open condition, which allows flowable material to pass through the port membrane 68. If the port membrane 68 is substantially flush with the plunger membrane 34, as in FIG. 8, then distal movement of the cannula or flowable material access member 72 moves the plunger membrane 34 to an open condition sequentially, but substantially simultaneously with the port membrane 68. On the other hand, if there is a small separation between the membranes 34 and 68, then distal relative movement of the tip of the cannula or flowable material access member 72 will move the port membrane 68 into an open condition, advance the tip of the cannula or flowable material access member 72 across the gap between the membranes 34 and 68, and then move the plunger membrane 34 into an open condition.

With the tip or distal end of the cannula or flowable material access member 72 extending through the two membranes 34 and 68 and at least partially positioned within the hollow plunger rod 30, the tip is moved further distally with respect to the syringe assembly 10 to press tip through the piston membrane 26 (FIG. 8). With at least the distal end or tip of the cannula or flowable material access member 72 positioned distally of the piston membrane 26 (i.e., within the syringe barrel 10), flowable material may be transferred between the flowable material receptacle 64 and the syringe assembly 10. If flowable material is to be transferred from the syringe assembly 10 to the flowable material receptacle 64, a vacuum may be created within the flowable material receptacle 64 (e.g., by proximal movement of a piston or the like within the body of the flowable material receptacle 64) to draw flowable material from the syringe barrel 12, through the cannula or flowable material access member 72, and into the flowable material receptacle 64. If flowable material is to be transferred from the flowable material receptacle 64 to the syringe assembly 10, then the pressure within the flowable material receptacle 64 may be increased (e.g., by distal movement of a piston or the like within the body of the flowable material receptacle 64) to cause flowable material to be ejected out of the flowable material receptacle 64 via the cannula or flowable material access member 72 and into the syringe barrel 12. In either case, it will be seen that the material transfer between the syringe assembly 10 and the flowable material receptacle 64 is sterile, without requiring a sterile weld or a filter or disinfection of either mating surface.

After material transfer, the syringe assembly 10 may be detached from the flowable material receptacle 64 by reverse relative rotation of the two to disengage the mating threads 20 and 66. It may be advantageous to move the cannula or flowable material access member 72 proximally away from the syringe assembly 10 to move the membranes 26, 34, and 68 into a closed condition and reposition the cannula or flowable material access member 72 inside of the flowable material receptacle 64 prior to disconnecting the syringe assembly 10 from the flowable material receptacle 64.

While the foregoing procedure included a port 62 of the flowable material receptacle 64 being secured to the external threads 20 of the barrel 12, a similar material transfer may be carried out without a threaded or secured connection between a syringe assembly and a proximal flowable material receptacle. In such an embodiment, the plunger membrane 34 is aligned with and pressed flat against the port membrane 68. The tip of the cannula or flowable material access member 72 may then be advanced distally with respect to the syringe assembly 10 until the tip traverses the membranes 68, 34, and 26 and enters into the syringe barrel 12, at which point material may be transferred between the syringe assembly 10 and the flowable material receptacle 64 as described above.

In syringe assemblies incorporating both a tip enclosure and a piston assembly having membranes, as in the illustrated embodiment, flowable material may be sterilely transferred between proximal and distal flowable material receptacles 64 and 54 using the syringe assembly 10 as an intermediary or adaptor. For example, material may be transferred from a distal flowable material receptacle 54 to a proximal flowable material receptacle 64 by first transferring the flowable material from the distal flowable material receptacle 54 to the syringe assembly 10 (as described above) and then from the syringe assembly 10 to the proximal flowable material receptacle 64 (as described above). Similarly, flowable material may be transferred from a proximal flowable material receptacle 64 to a distal flowable material receptacle 54 by first transferring the flowable material from the proximal flowable material receptacle 64 to the syringe assembly 10 (as described above) and then from the syringe assembly 10 to the distal flowable material receptacle 54 (as described above). In yet another example, flowable material may be transferred from one of the flowable material receptacles 54, 64 into the syringe assembly 10 and then an additional amount of flowable material (typically a different flowable material) may be transferred from the other flowable material receptacle 54, 64 into the syringe assembly 10 to mix the two flowable materials within the syringe barrel 12. The two material transfers in each procedure may be simultaneous or sequential, with sequential transfers being carried out either in quick succession or with the second transfer taking place much later than the first. During any one of these procedures, both flowable material receptacles 54 and 64 may be secured to the syringe assembly 10 during both transfers, or only one flowable material receptacle 54, 64 may be secured to the syringe assembly 10 during each transfer, or one flowable material receptacle 54, 64 may be secured to the syringe assembly 10 during one transfer and both flowable material receptacles 54 and 64 may be secured to the syringe assembly 10 during the other transfer. Any of a number of other flowable material transfers (e.g., transferring two flowable materials into the syringe assembly from separate proximal flowable material receptacles and then transferring the mixed materials into a distal flowable material receptacle) may also be facilitated using syringe assemblies according to the present disclosure.

In another embodiment, which is illustrated in FIGS. 9-15, a syringe assembly 100 may be provided generally in accordance with the foregoing description of the syringe assembly 10 of FIGS. 1-8, but with a modified tip enclosure and distal connector 102. The tip enclosure of FIG. 9 has a shroud 104 and a shroud membrane 106 associated with the connector 102 (e.g., at or adjacent to the proximal end of the connector 102), as in the embodiment of FIGS. 1-8, but the shroud 104 may be either flexible/deformable or rigid or semi-rigid, rather than flexible or deformable. As for the shroud membrane 106, it may be frangible to move from a closed condition to an open condition or otherwise configured to move between closed and open conditions, but the shroud membrane 106 may also be configured to remain in a closed condition (as in FIG. 2), without being movable to an open condition (as in FIG. 3). Furthermore, rather than being secured around its entire perimeter to the shroud or distal connector, only a portion of the perimeter or circumference of the shroud membrane 106 is fixedly secured (e.g., by an adhesive or the like) to the shroud 104 (if the shroud 104 is formed of a generally rigid material) or the distal connector 102.

The inner surface of the distal connector 102 (or of the shroud 104, if it is formed of a generally rigid material) may include a lateral projection 108 (FIG. 13) that is received within a lateral groove or cavity 110 defined in the perimeter or circumference of the shroud membrane 106. FIG. 13 illustrates a single lateral projection 108 received within the lateral groove 110, spaced away from the section of the membrane perimeter that is affixed to the distal connector 102 (which is located at the left side of the membrane 106 in the orientation of FIG. 13), but a plurality of lateral projections or a longer projection (e.g., an arcuate lip) may be provided to more securely retain the shroud membrane 106 in place. It may be advantageous for less than half of the perimeter of the shroud membrane 106 to be affixed to the connector 102 (or a rigid shroud 104), such as a 90° arc along the perimeter of the membrane 106 (in the case of a circular membrane), while the remainder of the membrane 106 is held in place across the connector 102 (or a rigid shroud 104) by the projection-groove arrangement to prevent material transfer through the connector 102, but it is also within the scope of the present disclosure for more than half of the perimeter of the shroud membrane 106 to be affixed to the connector 102 (or a rigid shroud 104).

In other embodiments, the projection-groove arrangement may be reversed, with the inner surface of the connector 102 (or of a rigid shroud 104) defining a groove or cavity, with the edge of the shroud membrane 106 or a projection from the perimeter of the shroud membrane 106 positioned within the groove to temporarily retain the shroud membrane 106 in place. Additionally, some other arrangement (e.g., an interference fit or a weak frangible connection) may replace the projection-groove arrangement to temporarily maintain the shroud membrane 106 in place.

Figures 9, 10:
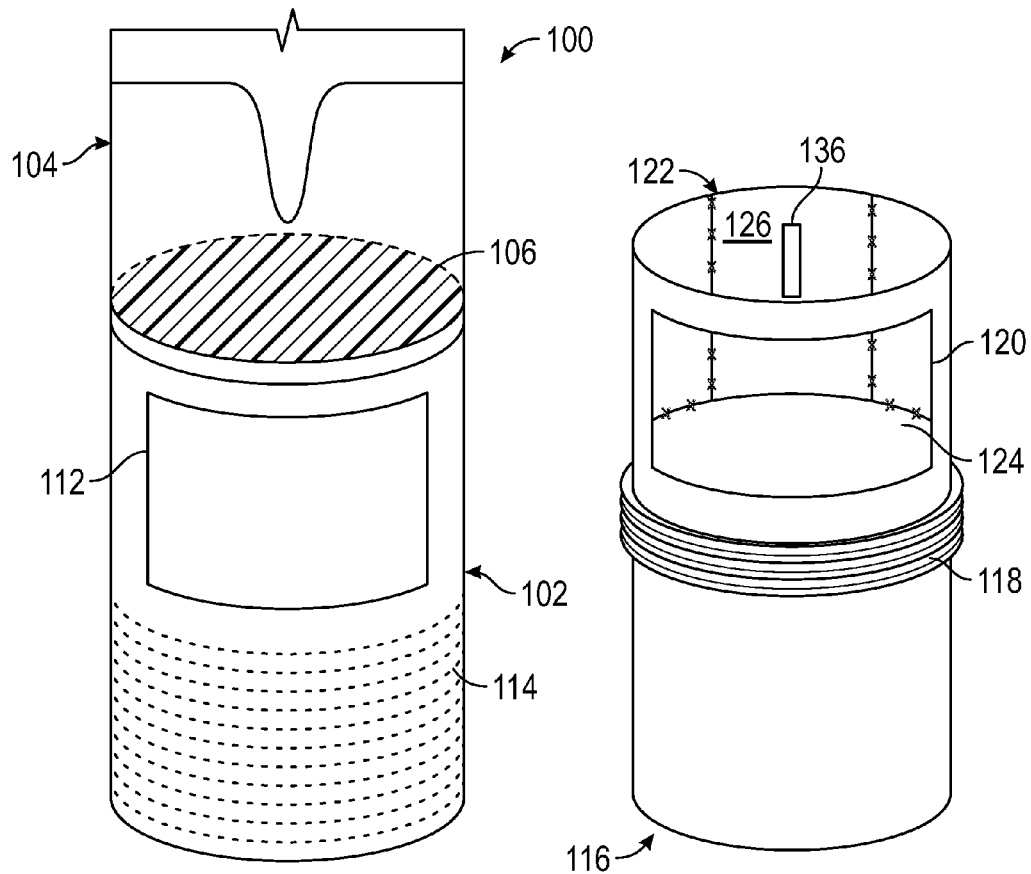
FIG. 9 is a perspective view of a distal portion of an alternative embodiment of a syringe assembly according to an aspect of the present disclosure.
FIG. 10 is a perspective view of a proximal portion of an adaptor that may be used in combination with the syringe assembly of FIG. 9.

The distal connector 102 of the syringe assembly 100 of FIG. 9 includes a lateral opening or window 112 positioned distally of the shroud membrane 106 and proximally of internal threads 114 of the connector 102 (if provided). At least a portion of the lateral opening 112 is angularly aligned with the portion of the shroud membrane 106 that is fixedly secured to the connector 102 (or a rigid shroud 104), while the portion of the shroud membrane 106 positioned opposite the lateral opening 112 (i.e., 180° away from the lateral opening 112) is movably associated with the inner surface of the connector 102 (or rigid shroud 104), such as by the aforementioned projection-groove arrangement. The lateral opening 112 of FIG. 9 is relatively large and rectangular, but it is within the scope of the present disclosure for the lateral opening to be differently sized and shaped.

A fluid-tight seal is defined around the lateral opening 112 to prevent the escape of flowable material out of the lateral opening 112, with a portion of the fluid-tight seal being defined by the portion of the membrane perimeter affixed to the connector 102 (or rigid shroud 104). To provide its portion of the fluid-tight seal, the affixed portion of the membrane 106 has an angular extent greater than the angular extent of the lateral opening 112. For example, if the lateral opening 112 is 60° wide, then the portion of the membrane perimeter affixed to the connector 102 (or rigid shroud 104) is greater than 60° wide, with the entire portion of the membrane perimeter angularly aligned with the lateral opening 112 (i.e., the part of the membrane 106 positioned directly above the lateral opening 112 in the orientation of FIG. 9) being affixed to the connector 102 (or rigid shroud 104) and with the affixed portion extending at least a nominal distance beyond the side edges of the lateral opening 112 (i.e. beyond the left and right edges of the lateral opening 112 in the orientation of FIG. 9). The other surfaces that combine with the affixed portion of the shroud membrane perimeter to define the fluid-tight seal will be described in greater detail herein.

FIG. 10 shows the proximal portion of an adaptor 116 configured for use in combination with the syringe assembly 100 of FIG. 9. The adaptor 116 is formed of a generally rigid material and has a proximal portion with a shape and configuration that are complementary to the shape and configuration of the distal connector 102. For example, in the illustrated embodiment, the proximal portion of the adaptor 116 is generally tubular, with an outer diameter that is slightly smaller than the inner diameter of the connector 102 (to allow the proximal portion of the adaptor 116 to be received within the connector 102) and external threads 118 that mate with the internal threads 114 of the connector 102. In other embodiments, the proximal portion of the adaptor may be differently shaped and configured depending on the shape and configuration of the distal connector of the associated syringe assembly.

Figure 14:
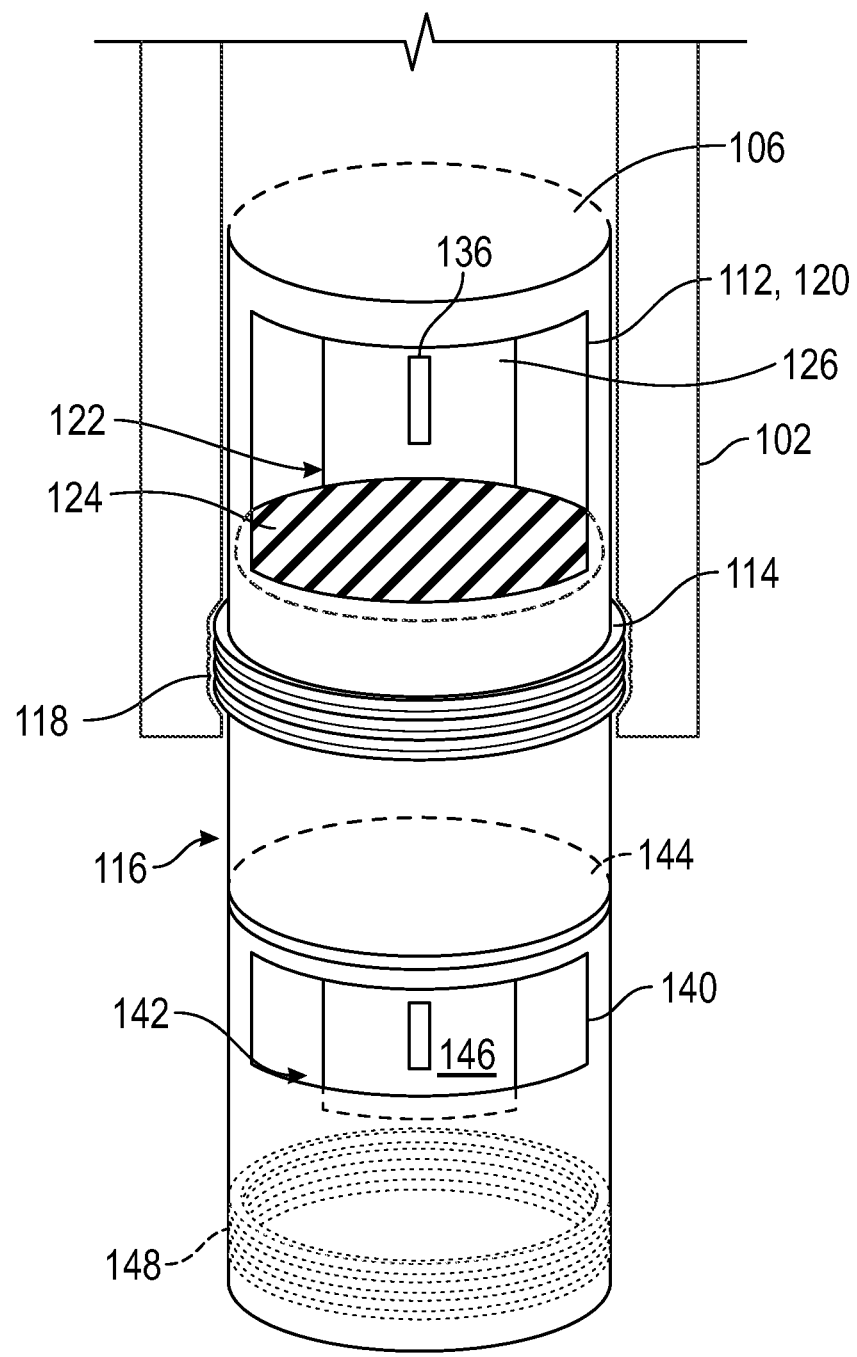
FIG. 14 is a perspective view of the syringe assembly of FIG. 9 connected to the adaptor of FIG. 10, with a portion of the syringe assembly omitted for illustrative purposes.

The adaptor 116 includes a lateral opening or window 120, which is configured to be at least partially aligned (but preferably substantially completely aligned) with the lateral opening or window 112 of the connector 102 when the syringe assembly 100 and adaptor 116 are connected (FIGS. 13 and 14). In one embodiment, the lateral opening or window 120 of the adaptor 116 is substantially identical to the lateral opening or window 112 of the connector 102, but it is also within the scope of the present disclosure for them to be differently sized and shaped.

A proximal adaptor membrane 122 is provided adjacent to the lateral window 120 of the adaptor 116 (FIGS. 10-14). The illustrated proximal adaptor membrane 122 has a configuration that is referred to herein as a "keyed membrane" configuration, while the shroud membrane 106 has a configuration that is referred to herein as a "flat membrane" configuration. In other embodiments, the configurations of the shroud membrane and adaptor membrane may be reversed, with the shroud membrane being a keyed membrane and the proximal adaptor membrane being a flat membrane, as in the embodiment of FIG. 17, which will be described in greater detail herein.

The proximal adaptor membrane 122 includes a radial portion 124 and an axial portion 126. In the illustrated embodiment, the radial and axial portions 124 and 126 are integrally formed (i.e., formed as a unitary component) of a deformable material, such as an elastomeric material (e.g., rubber). In other embodiments, the radial and axial portions 124 and 126 may be separately formed and secured together, either using the same or different materials for the two portions of the proximal adaptor membrane 122.

The radial portion 124 of the proximal adaptor membrane 122 may be configured according to the foregoing description of the shroud membrane 106, extending across the adaptor 116 to prevent material transfer therethrough. Only a portion of the perimeter or circumference of the radial portion 124 is fixedly secured (e.g., by an adhesive or the like) to the inner surface of the adaptor 116, while the remainder of the perimeter of the radial portion 124 is movably associated with the inner surface of the adaptor 116. The affixed portion of the perimeter forms another part of the fluid-tight seal that is defined around the lateral openings 112 and 120 to prevent the escape of flowable material out of the lateral openings 112 and 120. Similar to the affixed portion of the shroud membrane perimeter, the affixed portion of the radial portion perimeter has an angular extent greater than the angular extent of the lateral openings 112 and 120. In one embodiment, the same portions of the shroud membrane 106 and the radial portion 124 are affixed to the distal connector 102 (or rigid shroud 104) and adaptor 116, respectively (i.e., with the affixed portions having the same angular extent and being angularly aligned when the syringe assembly 100 has been secured to the adaptor 116).

In the illustrated embodiment, the portion of perimeter of the radial portion 124 that is affixed to the adaptor 116 corresponds to the portion of the perimeter of the radial portion 124 where the axial portion 126 is not present (i.e., the entire radial portion perimeter is affixed to the adaptor 116, except the part between the edges of the axial portion 126). FIG. 10 shows the part of the radial portion 124 that is affixed to the adaptor 116, with "X"s representing surfaces of the radial portion 124 that are affixed to the inner surface of the adaptor 116 (with the concealed part of the radial portion perimeter also being affixed to the adaptor 116). The corresponding portion of the perimeter of the shroud membrane 106 (i.e., the entire perimeter of the shroud membrane 106, except the part positioned between the edges of the of the axial portion 126 when the syringe assembly 100 has been secured to the adaptor 116) may be affixed to the inner surface of the connector 102.

In the illustrated embodiment, the inner surface of the adaptor 116 includes a lateral projection 128 (FIGS. 11 and 13) that is received within a lateral groove or cavity 130 defined in the perimeter or circumference of the radial portion 124. FIG. 13 illustrates a single lateral projection 128 received within the lateral groove 130, spaced away from the section of the radial portion perimeter that is affixed to the adaptor 116, but a plurality of lateral projections 128 or a longer projection (e.g., an arcuate lip) may be provided to more securely retain the radial portion 124 in place. As with the shroud membrane 106, it may be advantageous for less than half of the perimeter of the radial portion 124 to be affixed to the adaptor 116, such as a 90° arc along the perimeter of the radial portion 124 (in the case of a circular radial portion 124), while the remainder of the radial portion 124 is held in place across the adaptor 116 by the projection-groove arrangement to prevent material transfer through the adaptor 116, but it is also within the scope of the present disclosure for more than half of the perimeter of the radial portion 124 to be affixed to the adaptor 116.

In other embodiments, the projection-groove arrangement may be reversed, with the inner surface of the adaptor 116 defining a groove or cavity, with the edge of the radial portion 124 or a projection from the perimeter of the radial portion 124 positioned within the groove to temporarily retain the radial portion 124 in place. It is also within the scope of the present disclosure for some alternative arrangement (e.g., an interference fit or a weak frangible connection) to replace the projection-groove arrangement to temporarily maintain the radial portion 124 in place. In another embodiment, a projection-groove arrangement or the like between the axial portion 126 and the adaptor 116 may be sufficient to temporarily maintain both the radial portion 124 and the axial portion 126 in place. In yet another embodiment, both the radial portion and the axial portion of a keyed membrane may employ a projection-groove arrangement (as in FIG. 17) or the like to temporarily maintain the keyed membrane in place.

As for the axial portion 126, it extends between a fixed end, which is associated with the radial portion 124, and a free end. The axial portion 126 extends in an arc along the perimeter of the radial portion 124, directly adjacent to the inner surface of the adaptor 116. The axial portion 126 is affixed (e.g., by an adhesive or the like) to the inner surface of the adaptor 116 at and/or adjacent to its lateral edges. FIG. 10 shows the locations at which the axial portion 126 is affixed to the adaptor 116, with "X"s representing surfaces of the axial portion 126 that are affixed to the inner surface of the adaptor 116. The affixed portions of the axial portion 126, along with the affixed portions of the shroud membrane 106 and the radial portion 124 combine to define a fluid-tight seal around the lateral openings 112 and 120 when the syringe assembly 100 has been secured to the adaptor 116 to prevent the escape of flowable material out of the lateral openings 112 and 120 (FIG. 14). The part of the axial portion 126 between its edges (as with the part of the radial portion 124 and the shroud membrane 106 between the edges of the axial portion 126) are movably associated with the inner surface of the adaptor 116 (or of the connector 102 or rigid shroud 104, in the case of the shroud membrane 106) to allow selective movement of that part away from the adaptor wall, thereby selectively allowing material transfer through the adaptor 116, as will be described in greater detail.

The free end of the axial portion 126 may include an axial groove 132 defined therein. The axial groove 132 is configured to be complementary to an axial projection 134 of the shroud membrane 106 (FIG. 13). In the illustrated embodiment, the syringe assembly 100 is configured to be secured to the adaptor 116 by relative rotation and the mating threads 114 and 118. At least partially simultaneously with the threads 114 and 118 of the syringe assembly 100 and adaptor 116 mating together, the axial projection 134 may be rotated into the axial groove 132, which may be facilitated by an axial groove 132 having a generally helical shape. The axial groove 132 and axial projection 134 may have trapezoidal cross-sectional shapes, as shown in FIG. 13, to form a dovetail joint, which resists the two from separating upon movement of the shroud membrane 106 and axial portion 126 away from each other. By such a configuration, the conjoined regions of the shroud membrane 106 and axial portion 126 may be moved together as a unit to selectively allow material transfer through the adaptor 116, as will be described in greater detail. It should be understood that the illustrated groove-projection arrangement is merely exemplary and that other arrangements for associating the shroud membrane 106 and the axial portion 126 of the proximal adaptor membrane 122 may be employed without departing from the scope of the present disclosure. Preferably, the joinder arrangement is secure when the syringe assembly 100 is secured to the adaptor 116, but releasable after completion of a material transfer application when the syringe assembly 100 and the adaptor 116 are detached from each other.

The axial portion 126 includes a formation or feature 136 that allows the axial portion 126 to be engaged and moved away from the inner surface of the adaptor 116. In the illustrated embodiment, the formation or feature 136 is provided as a keyway, which is a cavity or indentation in the surface of the axial portion 126 facing toward the center of the adaptor 116 (FIG. 11). As will be described in greater detail herein, the axial portion 126 provides a portion of a fluid-tight seal around an associated lateral opening 120, such that the keyway 136 preferably has depth less than the thickness of the axial portion 126 (as best illustrated in FIGS. 11 and 13) if provided as a cavity or indentation to avoid providing a flow passage through the axial portion 126.

Figures 18, 19:
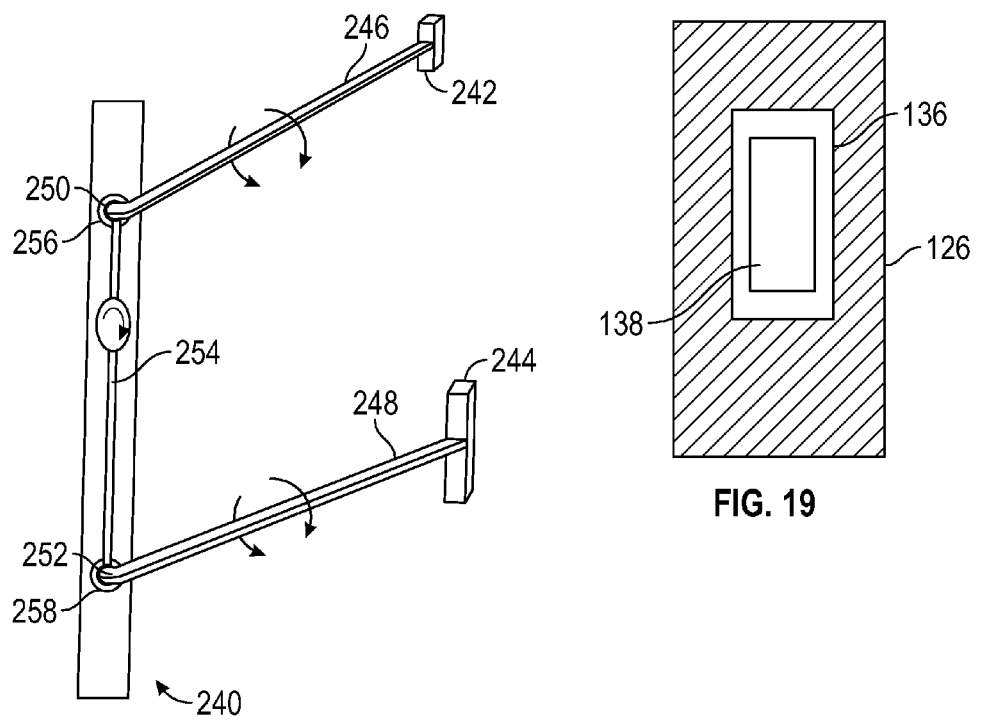
FIG. 18 is a perspective view of an exemplary keying tool for engaging keyways of the proximal and distal keyed membranes of FIG. 17.
FIG. 19 is a front elevational view of a key of the keying tool of FIG. 18 positioned within a keyway of a keyed membrane.
Figures 19A, 20, 20A:
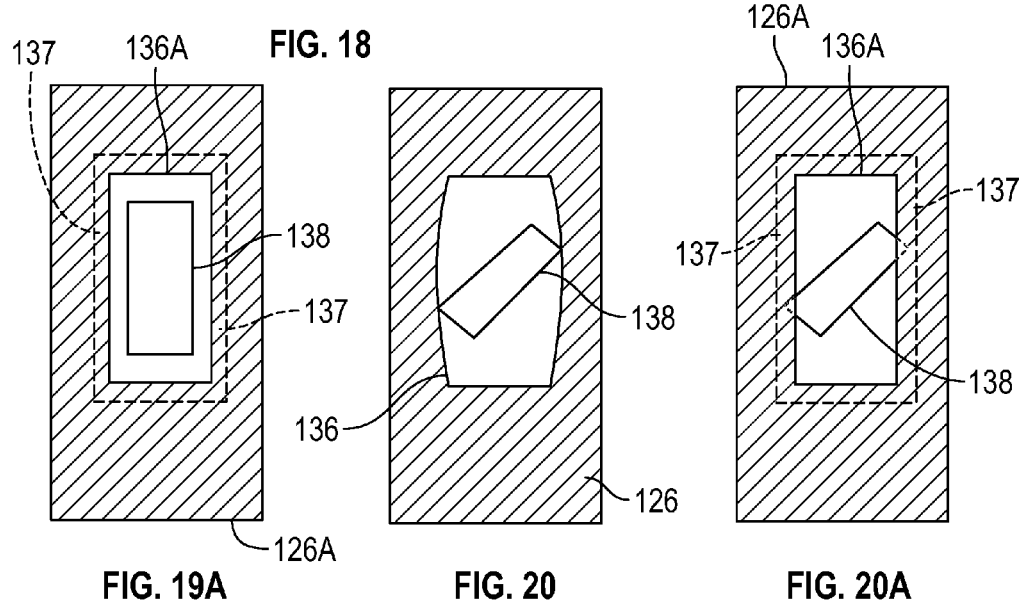
FIG. 19A is a front elevational view of an alternative embodiment of a keyway of a keyed membrane.
FIG. 20 is a front elevational view of the key and keyway of FIG. 19, with the key rotated to grip the keyway.
FIG. 20A is a front elevational view of the keyway of FIG. 19A, with the key of a keying tool rotated to fit within grooves of the keyway.

As described above, the axial portion 126 (including the keyway 136) is formed of a deformable or flexible material (e.g., an elastomer), which allows the keyway 136 to be deformed from an initial configuration (FIG. 19) to a deformed configuration (FIG. 20). In use, a tool is inserted through the lateral openings 112 and 120 to position a gripper end 138 of the tool within the keyway 136 (FIG. 19). The tool is then rotated to rotate portions of the gripper end 138 into engagement with opposing sides of the keyway 136 (FIG. 20), thereby wedging the gripper end 138 between the opposing sides. With the gripper end 138 wedged against the opposing sides of the keyway 136, the tool may be withdrawn through the lateral openings 112 and 120, which moves the gripper end 138 toward the lateral openings 112 and 120. The keyway 136 (and, hence the portion of the axial portion 126 not affixed to the adaptor wall) will move away from the adaptor wall with the gripper end 138 while the shroud membrane 106 and radial portion 124 deform or flex (as in FIG. 22), thereby allowing material transfer through the adaptor 116, between the axial portion 126 and the associated portion of the adaptor wall (as will be described in greater detail).

The illustrated keyway 136 is merely exemplary, as the axial portion 126 may include differently configured formations or features without departing from the scope of the present disclosure. For example, FIGS. 19A and 20A show another embodiment, in which the axial portion 126A of a keyed membrane includes a keyway 136A having opposing sides which define grooves 137 that allow portions of an appropriately configured gripper end 138 to be rotated into (from the orientation of FIG. 19A to the orientation of FIG. 20A) without deforming the keyway 136A. With these portions of the gripper end 138 positioned within the grooves 137 (as in FIG. 20A), the tool may be withdrawn through the lateral openings 112 and 120, which causes the gripper end 138 to bear against surfaces of the axial portion 126A or keyway 136A overlaying the grooves 137, thereby moving the gripper end 138 (along with the keyway 136A and axial portion 126A) toward the lateral openings 112 and 120, thereby allowing material transfer between the axial portion 126A and the inner surface of the adaptor 116. In another embodiment, the formation or feature of the axial portion 126 may be a projection, rather than a cavity or indentation. In one embodiment employing a projection, the formation or feature may be a loop or a hook that may be engaged by a hook-shaped end of a tool (or by the fingers of a user). With the tool/fingers hooked onto the loop/hook, the tool/fingers may be withdrawn through the lateral openings 112 and 120 to move the axial portion 126 toward the lateral openings 112 and 120, thereby allowing material transfer between the axial portion 126 and the inner surface of the adaptor 116. Other arrangements for moving the axial portion 126 away from the wall of the adaptor 116 may also be employed without departing from the scope of the present disclosure.

Figure 15:
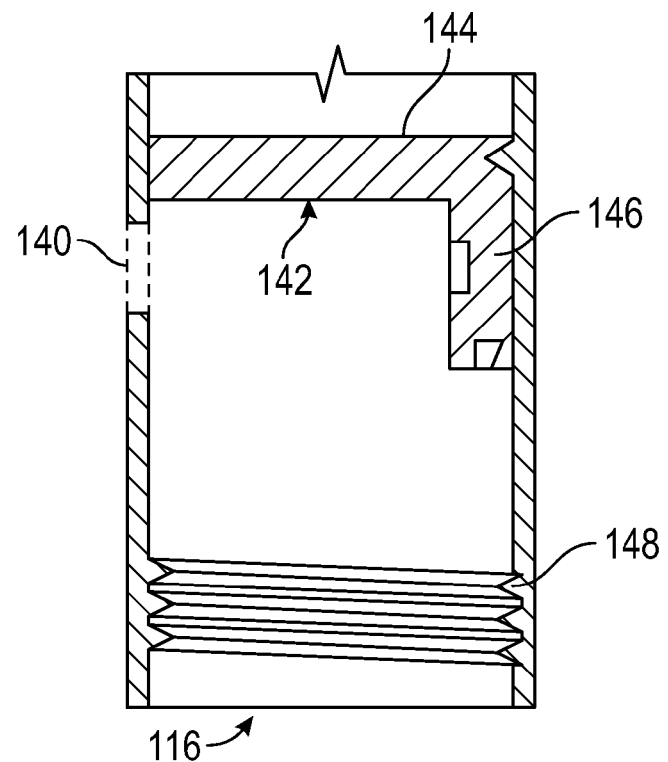
FIG. 15 is a cross-sectional side elevational view of a distal portion of the adaptor of FIG. 10.

FIGS. 14 and 15 show a distal portion of the adaptor 116. In the illustrated embodiment, the distal portion of the adaptor 116 may be considered to be a mirror image of the proximal portion, with a lateral opening 140 and associated distal adaptor membrane 142 having a radial portion 144 and an axial portion 146. Preferably, the distal lateral opening 140 of the adaptor 116 is substantially angularly aligned with the proximal lateral opening 120, as shown in FIG. 14, but they may be positioned at different locations along the adaptor wall. The two lateral openings 120 and 140 of the adaptor 116 may be identical or differently shaped and sized.

As a mirror image of the proximal portion, the radial portion 144 of the distal adaptor membrane 142 is positioned proximally of the associated lateral opening 140. Although not illustrated, the distal portion of the adaptor 116 is configured to be secured to the port of a flowable material receptacle having a port membrane provided as a mirror image of the shroud membrane 106. When the adaptor 116 and port are secured together (using internal threads 148 of the adaptor 116 and external threads of the port in the illustrated embodiment), the distal adaptor membrane 142 and port membrane combine to form a distal flowable material control mechanism that forms a fluid-tight seal around the distal lateral opening 140 of the adaptor 116 in the same way that the proximal adaptor membrane 122 and the shroud membrane 106 combine to form a proximal material transfer control mechanism (as described above and shown in FIG. 13).

Figure 16:
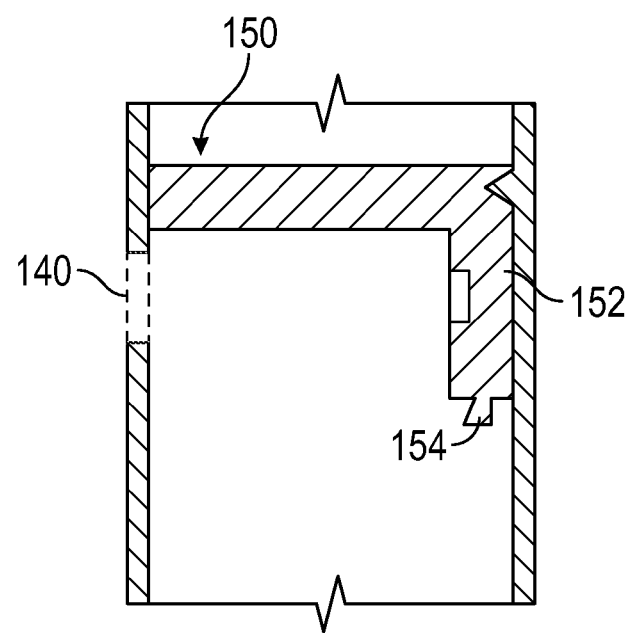
FIG. 16 is a cross-sectional side elevational view of an alternative embodiment of a distal keyed membrane of the adaptor of FIG. 10.

While FIGS. 14 and 15 illustrate an embodiment in which the distal portion of the adaptor 116 is provided as a mirror image of the proximal portion, it is within the scope of the present disclosure for the distal portion or any component thereof to be differently configured from the corresponding member of the proximal portion of the adaptor 116. For example, FIG. 16 illustrates a distal adaptor membrane 150 having an axial portion 152 with an axial projection 154 that mates with a complementary axial groove of a port membrane when the adaptor 116 is secured to the port of a flowable material receptacle. It should be understood that this same configuration may be applied to the proximal material transfer control mechanism, with the axial portion 126 of the proximal adaptor membrane 122 having an axial projection and the distal face of the shroud membrane 106 having a complementary axial groove.

Figure 17:
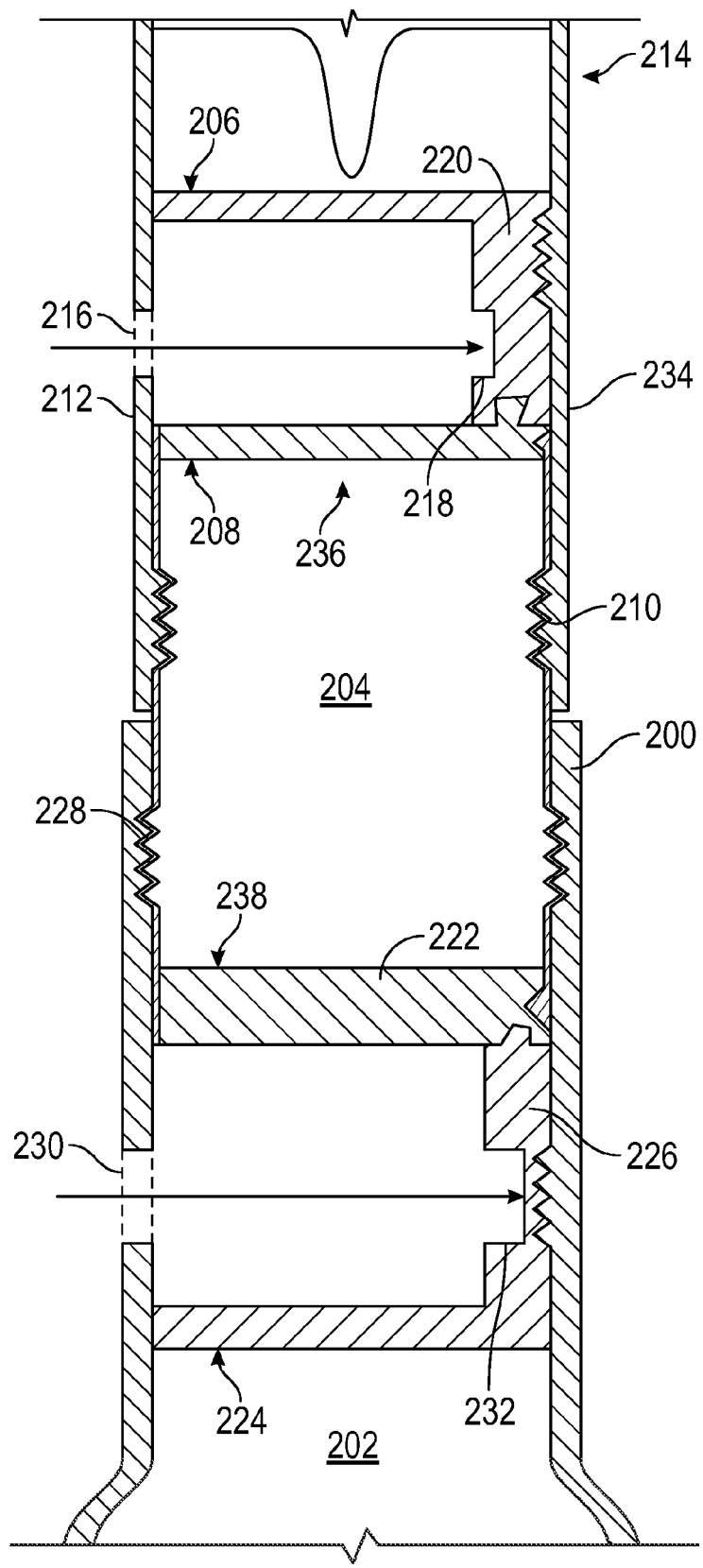
FIG. 17 is cross-sectional side elevational view of an alternative embodiment of an adaptor connected to an alternative embodiment of a syringe assembly and a flowable material receptacle port.

FIG. 17 shows a variation of the syringe assembly 100 and adaptor 116 of FIG. 14, with the port 200 of a flowable material receptacle 202 connected to a distal portion of the adaptor 204. In contrast to the embodiment of FIG. 14, the shroud membrane 206 is provided as a keyed membrane (similar to either of the adaptor membranes 122 and 142 described above), rather than as a flat membrane (similar to the shroud membrane 106 described above). In particular, the shroud membrane 206 of FIG. 17 is provided in accordance with the foregoing description of the distal adaptor membrane 142 of FIG. 15. As each material transfer control mechanism includes the combination of a keyed membrane and a flat membrane, the proximal adaptor membrane 208 is provided as a flat membrane (similar to the shroud membrane 106 of FIGS. 13 and 14), but with an axial projection positioned on a proximal face of the proximal adaptor membrane 208 to mate with a distal axial groove of the shroud membrane 206. In such an embodiment, the proximal adaptor membrane 208 may be located at or adjacent to the proximal end of the adaptor 204, proximally of proximal external threads 210 of the adaptor 204. Additionally, the proximal portion of the adaptor 204 may be provided without a lateral opening, with only the distal connector 212 of the syringe assembly 214 having a lateral opening 216 configured to allow the keyway 218 of the axial portion 220 of the shroud membrane 206 to be accessed therethrough.

The distal portion of the illustrated adaptor 204 includes a distal adaptor membrane 222 provided as a flat membrane, with an axial groove defined in the distal face of the distal adaptor membrane. As each material transfer control mechanism includes the combination of a keyed membrane and a flat membrane, the port membrane 224 is provided as a keyed membrane, which may be similar to the proximal adaptor membrane 122 described above, but with an axial projection positioned at the free end of the axial portion 226 of the port membrane 224 to mate with the axial groove of the distal adaptor membrane 222. Similar to the proximal portion of the adaptor 204, the distal adaptor membrane 222 may be located at or adjacent to the distal end of the adaptor 204, distally of distal external threads 228 of the adaptor 204. Additionally, the distal portion of the adaptor 204 may be provided without a lateral opening, with only the port 200 of the flowable material receptacle 202 having a lateral opening 230 configured to allow the keyway 232 of the axial portion 226 of the port membrane 224 to be accessed therethrough.

While the illustrated embodiments provide an adaptor with a pair of keyed membranes (with the associated shroud membrane and port membrane being provided as flat membranes) or a pair of flat membranes (with the associated shroud membrane and port membrane being provided as key membranes), alternative embodiments are also possible. For example, the proximal adaptor membrane may be provided as a keyed membrane (with the associated shroud membrane being provided as a mating flat membrane) and the distal adaptor membrane being provided as a flat membrane (with the associated port membrane being provided as a mating keyed membrane). In yet another embodiment, the proximal adaptor membrane may be provided as a flat membrane (with the associated shroud membrane being provided as a mating keyed membrane) and the distal adaptor membrane being provided as a keyed membrane (with the associated port membrane being provided as a mating flat membrane). In different embodiments, it may be appropriate for the adaptor to have a pair of lateral openings, only one lateral opening (either defined at the proximal portion of the adaptor or at the distal portion of the adaptor), or no lateral openings.

In use, the proximal portion of the adaptor 204 is secured to the distal connector 234 of syringe assembly 214 and the distal portion of the adaptor 204 is secured to the port 200 of the flowable material receptacle 202 to define a transfer passage. The adaptor 204 may be secured to the syringe assembly 214 before being secured to the flowable material receptacle 202 or may be secured to the flowable material receptacle 202 before being secured to the syringe assembly 214 or may be secured to the syringe assembly 214 and the flowable material receptacle 202 substantially simultaneously.

With the adaptor 204 connected to the syringe assembly 214 and the flowable material receptacle 202, the shroud membrane 206 and the proximal adaptor membrane 208 combine to define a proximal material transfer control mechanism 236, while the port membrane 224 and the distal adaptor membrane 222 combine to define a distal material transfer control mechanism 238. Each material transfer control mechanism 236, 238 prevents material transfer between the syringe assembly 214 and the flowable material receptacle 202 via the transfer passage, and both material transfer control mechanisms 236 and 238 must be actuated to allow material transfer through the transfer passage. The material transfer control mechanisms 236 and 238 may be actuated sequentially (e.g., with the proximal material transfer control mechanism 236 being actuated prior to the distal material transfer control mechanism 238 or with the distal material transfer control mechanism 238 being actuated prior to the proximal material transfer control mechanism 236) or may be actuated substantially simultaneously.

Figure 21:
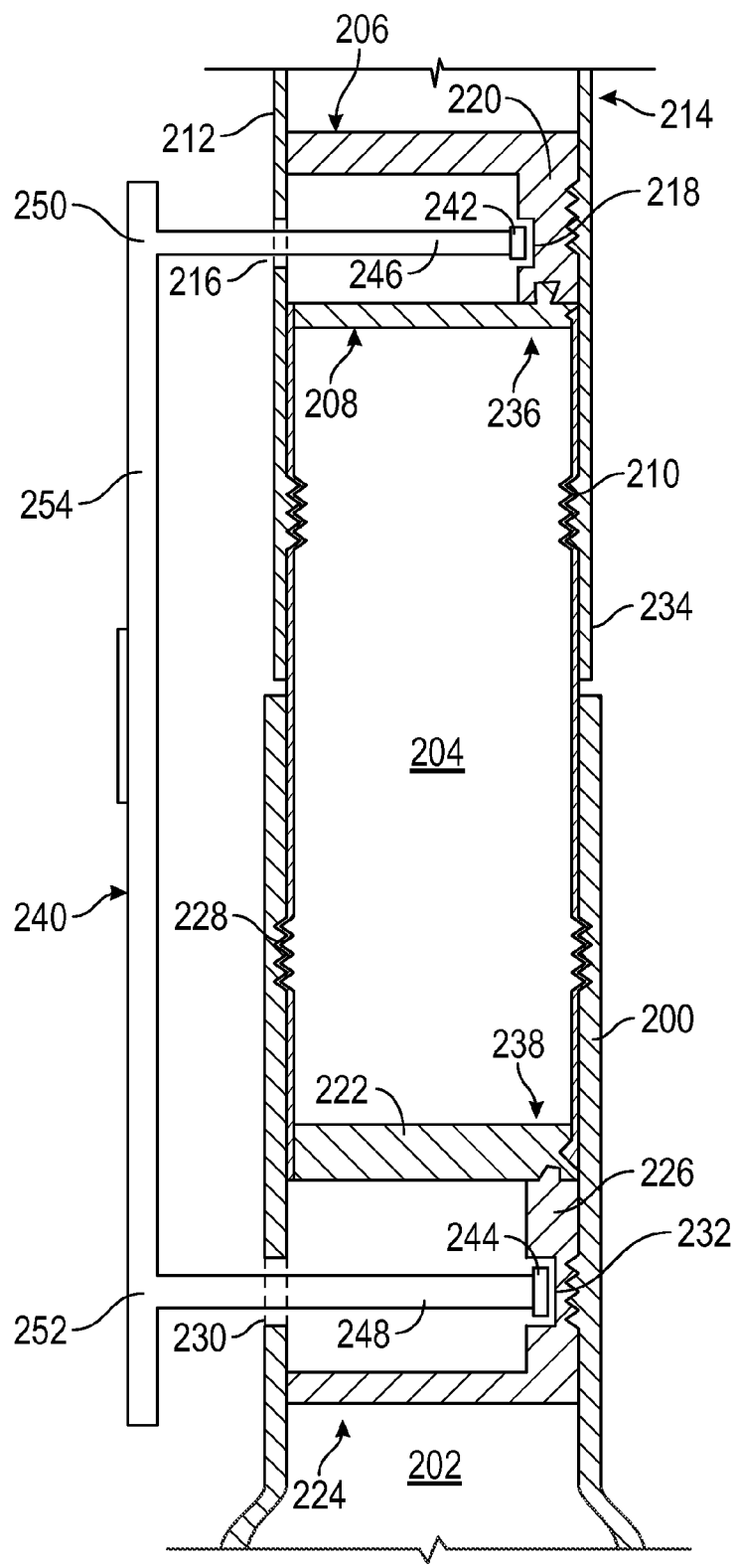
FIG. 21 is a cross-sectional side elevational view of the keying tool of FIG. 18 engaging the keyways of the proximal and distal keyed membranes of FIG. 17.
Figure 22:
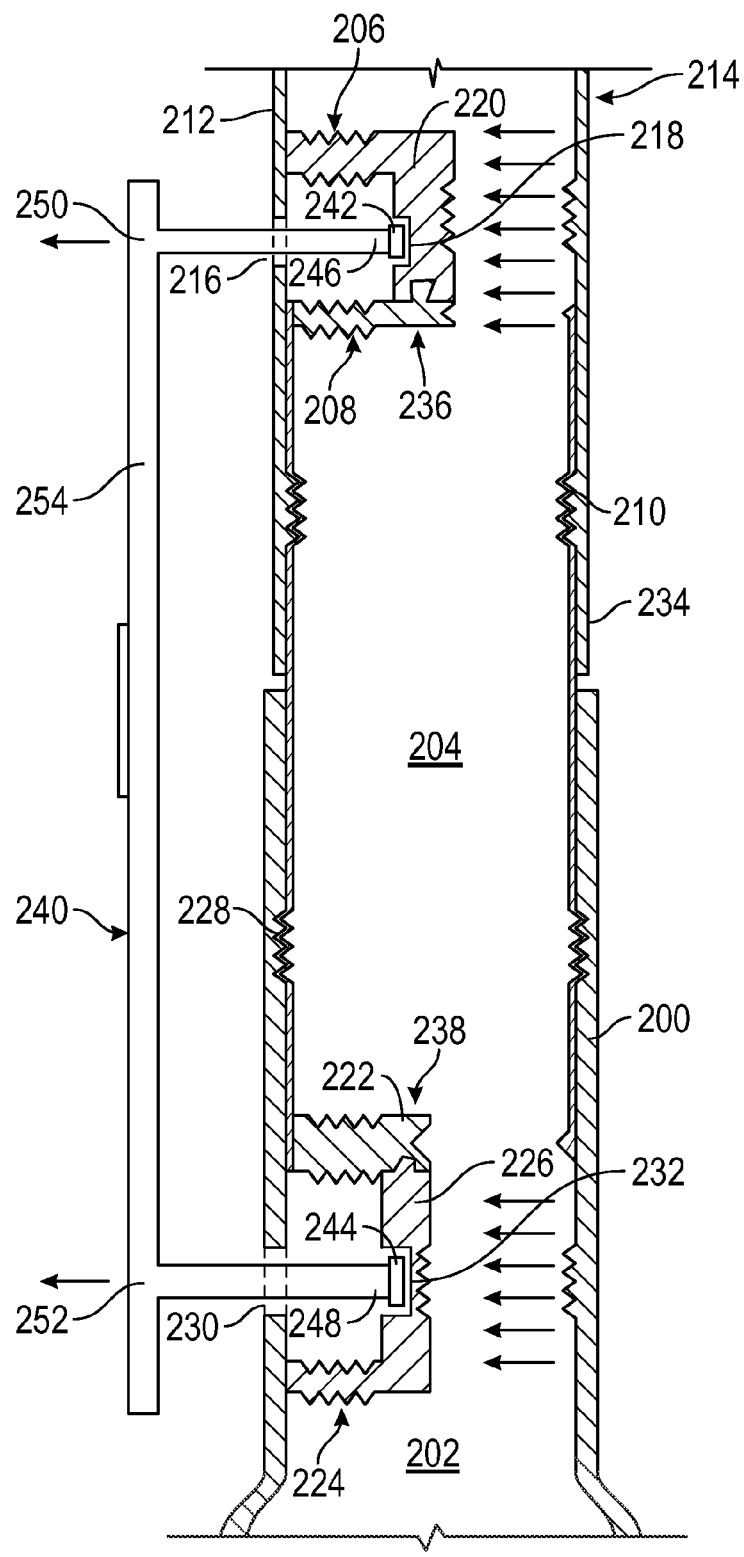
FIG. 22 is a cross-sectional side elevational view of the keying tool of FIG. 18 deforming or flexing the proximal and distal keyed membranes and flat membranes of FIG. 17 to allow material transfer between the syringe assembly and the flowable material receptacle.

The material transfer control mechanisms 236 and 238 may be actuated using separate tools or with a single tool. FIGS. 21 and 22 illustrate the two material transfer control mechanisms 236 and 238 being actuated substantially simultaneously using a keying tool 240, which is illustrated in FIG. 18. The exemplary keying tool 240 is provided with a proximal gripper end or member 242 and a distal gripper end or member 244. Each gripper end 242, 244 is configured to be at least partially positioned within the associated keyway 218, 232, as in FIGS. 19 and 21. Each gripper end 242, 244 includes an associated lateral shaft 246, 248 that is sufficiently elongated to position the associated gripper end 242, 244 within the associated keyway 218, 232 while the end 242, 244 of the lateral shaft 246, 248 opposite the gripper end 242, 244 is positioned outside of the transfer passage. The ends 250 and 252 of the lateral shafts 246 and 248 positioned outside of the transfer passage are associated with a third shaft 254 by gear assemblies 256 and 258, respectively, or a comparable joint that allows the third shaft 254 to rotate the lateral shafts 246 and 248. In the illustrated embodiment, each gear assembly 256, 258 is provided as a worm-worm gear arrangement, by which rotation of the third shaft 254 around its central axis causes rotation of the lateral shafts 246 and 248 around their central axes (which are substantially perpendicular to the third shaft 254).

In use, the lateral shafts 246 and 248 of the keying tool 240 are inserted through the lateral openings 216 and 230 to position their gripper ends 242 and 244 at least partially within the keyway 218, 232 of the associated material transfer control mechanism 236, 238. The third shaft 254 of the keying tool 240 is then rotated about its central axis to rotate the lateral shafts 246 and 248 about their central axes, thereby rotating the gripper ends 242 and 244 into engagement with opposing sides of the associated keyway 218, 232 (as in FIG. 20), which wedges each gripper end 242, 244 between the opposing sides. With the gripper ends 242 and 244 wedged against the opposing sides of the associated keyway 218, 232, the keying tool 240 may be withdrawn through the lateral openings 216 and 230, which moves the gripper ends 242 and 244 toward the lateral openings 216 and 230 (FIG. 22). The keyways 218 and 232 (and, hence the portions of the material transfer control mechanisms 236 and 238 not affixed to the transfer passage) will move away from the transfer passage wall with the gripper ends 242 and 244, thereby allowing sterile material transfer past each material transfer control mechanism 236, 238. Each material transfer control mechanism 236, 238 is sealed around the associated lateral opening 216, 230, allowing material transfer through the transfer passage between the syringe assembly 214 and the flowable material receptacle 202 without leakage from either lateral opening 216, 230.

After material transfer between the syringe assembly 214 and the material transfer receptacle 202 has been completed, the keying tool 240 may be moved in the opposite direction (i.e., from the position of FIG. 22 to the position of FIG. 21) to return the material transfer control mechanisms 236 and 238 to their initial positions, thereby preventing additional material transfer through the transfer passage. The third shaft 254 of the keying tool 240 may then be rotated to disengage the gripper ends 242 and 242 from the associated keyway 218, 232 (i.e., moving the gripper ends 242 and 244 from the orientation of FIG. 20 to the orientation of FIG. 19), with the keying tool 240 being moved away from the adaptor 204 to withdraw the gripper ends 242 and 244 from the transfer passage. Finally, the adaptor 204 may be disconnected from the syringe assembly 214 and flowable material receptacle 202 and either discarded or sterilized for repeated use. Alternatively, one of the syringe assembly 214 and the flowable material receptacle 202 may remain connected to the adaptor 204 while a third device is connected to the opposing end of the adaptor 204 for an additional material transfer application.

It will be understood that the embodiments described above are illustrative of some of the applications of the principles of the present subject matter. Numerous modifications may be made by those skilled in the art without departing from the spirit and scope of the claimed subject matter, including those combinations of features that are individually disclosed or claimed herein. For these reasons, the scope hereof is not limited to the above description but is as set forth in the following claims, and it is understood that claims may be directed to the features hereof, including as combinations of features that are individually disclosed or claimed herein.

The invention claimed is:

1. A syringe assembly comprising:
   a barrel extending between proximal and distal ends and defining a chamber to contain flowable materials;
   a tip associated with the distal end of the barrel;
   a piston movable within the chamber;
   a hollow plunger rod extending between proximal and distal ends and defining a lumen configured to accommodate the flow of said flowable materials between the proximal and distal ends of the plunger rod, wherein the distal end of the plunger rod is associated with the piston;
   a plunger positioned outside of the chamber and associated with the proximal end of the plunger rod;
   a two-way piston membrane associated with the piston, at least partially aligned with the distal end of the plunger rod, and movable from a closed condition to an open condition to allow two way flow therethrough;
   a two-way plunger membrane associated with the plunger, at least partially aligned with the proximal end of the plunger rod, and movable from a closed condition to an open condition to allow two way flow therethrough, wherein at least a portion of the piston membrane and/or at least a portion of the plunger membrane is positioned within the lumen of the plunger rod;
   a flexible shroud extending between proximal and distal ends, wherein the proximal end of the flexible shroud is directly connected to the barrel and/or the tip, with the flexible shroud surrounding the tip and the distal end of the flexible shroud positioned distally of the tip; and
   a shroud membrane associated with the distal end of the flexible shroud and movable from a closed condition to an open condition.

2. The syringe assembly of claim 1, wherein the shroud membrane is movable between the closed condition and the open condition.

3. The syringe assembly of claim 1, further comprising a generally rigid connector associated with the distal end of the flexible shroud and/or the shroud membrane.

4. The syringe assembly of claim 3, wherein an outer surface of the flexible shroud has a diameter substantially equal to a diameter of an outer surface of the connector.

5. The syringe assembly of claim 3, wherein an inner surface of the connector includes internal threads.

6. The syringe assembly of claim 1, wherein the piston membrane is movable between the closed condition and the open condition.

7. The syringe assembly of claim 1, wherein the plunger membrane is movable between the closed condition and the open condition.

8. The syringe assembly of claim 1, wherein the piston membrane and/or the plunger membrane comprises a slit membrane with a slit configured to be moved between the closed and open conditions.

9. The syringe assembly of claim 1, wherein the piston membrane includes a frangible section configured to be broken to move the piston membrane from the closed condition to the open condition.

10. The syringe assembly of claim 1, wherein the piston membrane and the plunger membrane are substantially identical.

11. The syringe assembly of claim 1, wherein the shroud membrane comprises a slit membrane with a slit configured to be moved between the closed and open conditions.

12. The syringe assembly of claim 1, wherein an outer surface of the flexible shroud has a diameter substantially equal to a diameter of an outer surface of the distal end of the barrel.

13. The syringe assembly of claim 1, wherein an outer surface of the barrel includes external threads.

14. A syringe assembly comprising:
   a barrel extending between proximal and distal ends and defining a chamber to contain flowable materials;
   a tip associated with the distal end of the barrel;
   a piston movable within the chamber;
   a hollow plunger rod extending between proximal and distal ends and defining a lumen configured to accommodate the flow of said flowable materials between the proximal and distal ends of the plunger rod, wherein the distal end of the plunger rod is associated with the piston;
   a plunger positioned outside of the chamber and associated with the proximal end of the plunger rod;
   a two-way piston membrane associated with the piston, at least partially aligned with the distal end of the plunger rod, and movable from a closed condition to an open condition to allow two way flow therethrough; and
   a two-way plunger membrane associated with the plunger, at least partially aligned with the proximal end of the plunger rod, and movable from a closed condition to an open condition to allow two way flow therethrough, wherein at least a portion of the piston membrane and/or at least a portion of the plunger membrane is positioned within the lumen of the plunger rod.

15. The syringe assembly of claim 14, wherein the piston membrane is movable between the closed condition and the open condition.

16. The syringe assembly of claim 14, wherein the plunger membrane is movable between the closed condition and the open condition.

17. The syringe assembly of claim 14, wherein the piston membrane and/or the plunger membrane comprises a slit membrane with a slit configured to be moved between the closed and open conditions.

18. The syringe assembly of claim 14, wherein the piston membrane includes a frangible section configured to be broken to move the piston membrane from the closed condition to the open condition.

19. The syringe assembly of claim 14, wherein the piston membrane and the plunger membrane are substantially identical.

* * * * *